(12) United States Patent
Burton

(10) Patent No.: US 6,397,845 B1
(45) Date of Patent: Jun. 4, 2002

(54) APPARATUS FOR GAS DELIVERY

(75) Inventor: David Burton, Camberwell (AU)

(73) Assignee: Compumedics, Ltd., Abbotsford (AU)

( * ) Notice: Subject to any disclaimer, the term of this patent is extended or adjusted under 35 U.S.C. 154(b) by 0 days.

(21) Appl. No.: 09/066,421

(22) PCT Filed: Oct. 31, 1996

(86) PCT No.: PCT/AU96/00679

§ 371 Date: Dec. 8, 1998

(87) PCT Pub. No.: WO97/16216

PCT Pub. Date: May 9, 1997

(30) Foreign Application Priority Data

Oct. 31, 1995 (AU) .......................... PN 6273

(51) Int. Cl.$^7$ .......................... A61M 16/00; A62B 7/00; F16K 31/02
(52) U.S. Cl. ........................... 128/204.23; 128/204.18; 128/204.21; 128/204.26
(58) Field of Search ..................... 128/204.18, 204.21, 128/204.23, 204.26; 600/529, 533, 534

(56) References Cited

U.S. PATENT DOCUMENTS 4,444,201 A * 4/1984 Itoh .......................... 128/716
5,047,930 A * 9/1991 Martens et al. ........ 364/413.04

(List continued on next page.)

FOREIGN PATENT DOCUMENTS

| AU | 3387793 | 4/1993 | |
| AU | 7764194 | 5/1995 | |
| AU | 3067895 | 11/1995 | |
| EP | 0651971 | 5/1995 | |
| WO | 8810108 | 12/1988 | |
| WO | 9113575 | 9/1991 | |
| WO | 9211054 | 7/1992 | .......... A61M/16/00 |
| WO | 9222244 | 12/1992 | |
| WO | 9416610 | 8/1994 | |
| WO | 9423780 | 10/1994 | |
| WO | 9532016 | 11/1995 | |
| WO | 9533403 | 12/1995 | |

OTHER PUBLICATIONS

Nadel et al., Text book of Respirtory Medicine 2nd Ed. vol. 2, Chap. pp. 2301–2324.*

Principles and Practice of Sleep Medicine, Meir H. Kryger, Thomas Roth, and William C. Dement (eds.), 1994, pp. 943–960 and 984–993.

*Primary Examiner*—John G. Weiss
*Assistant Examiner*—Joseph F. Weiss, Jr.
(74) *Attorney, Agent, or Firm*—Fulbright & Jaworski L.L.P.

(57) ABSTRACT

An apparatus for controlling gas delivery to a patient is disclosed, wherein delivery is adapted to maintain a physiological sleep state. The apparatus includes a monitoring device that monitors EEG, EOG, EMG, patient position and patient breathing. The apparatus also contains a microprocessor, which is programmed to derive sleep state specific indicators from the data received by the monitoring device and to determine if the sleep state is in a stable or deteriorating phase, where upon gas pressure will be automatically adjusted to maintain the sleep state if desired. The microprocessor is programmed with a unique automatic sleep staging algorithm and a gas pressure seek algorithm which work together to automatically adjust delivered respiratory gas pressure to a user based upon the determined sleep state and the sleep states condition.

28 Claims, 18 Drawing Sheets

U.S. PATENT DOCUMENTS

| | | | |
|---|---|---|---|
| 5,134,995 A | * 8/1992 | Gruenke et al. | 128/204.23 |
| 5,148,802 A | 9/1992 | Sanders | |
| 5,188,098 A | 2/1993 | Hoffman et al. | 128/204.23 |
| 5,199,424 A | * 4/1993 | Sullivan et al. | 128/204.18 |
| 5,203,343 A | * 4/1993 | Axe et al. | 128/725 |
| 5,239,995 A | 8/1993 | Estes | |
| 5,245,995 A | * 9/1993 | Sullivan et al. | 128/204.23 |
| 5,259,373 A | * 11/1993 | Gruenke et al. | 128/204.23 |
| 5,259,390 A | * 11/1993 | MacLean | 128/515 |
| 5,280,791 A | * 1/1994 | Lavie | 600/544 |
| 5,313,937 A | 5/1994 | Zdrojkowski | |
| 5,335,654 A | * 8/1994 | Rapoport | 128/204.23 |
| 5,353,788 A | * 10/1994 | Miles | 128/204.23 |
| 5,433,193 A | 7/1995 | Sanders | |
| 5,458,137 A | * 10/1995 | Axe et al. | 128/204.23 |
| 5,464,012 A | * 11/1995 | Falcone | 128/630 |
| 5,485,851 A | * 1/1996 | Erickson | 128/716 |
| 5,490,502 A | * 2/1996 | Rapoport et al. | 128/204.23 |
| 5,520,192 A | * 5/1996 | Kitney et al. | 128/716 |
| 5,522,382 A | * 6/1996 | Sullivan et al. | 128/204.23 |
| 5,535,738 A | * 7/1996 | Estes et al. | 128/204.23 |
| 5,535,739 A | * 7/1996 | Rapoport et al. | 128/204.23 |
| 5,546,933 A | * 8/1996 | Rapoport et al. | 128/204.23 |
| 5,549,106 A | 8/1996 | Gruenke | |
| 5,551,418 A | * 9/1996 | Estes et al. | 128/204.23 |
| 5,551,419 A | * 9/1996 | Froehlich et al. | 128/204.23 |
| 5,645,053 A | * 7/1997 | Remmers et al. | 128/204.23 |
| 5,704,345 A | * 1/1998 | Berthon-Jones | 128/204.23 |
| 5,749,366 A | * 5/1998 | Odagiri et al. | 600/515 |
| 5,823,187 A | * 10/1998 | Estes et al. | 128/204.23 |
| 5,845,636 A | * 12/1998 | Gruenke et al. | 128/204.23 |
| 5,901,704 A | * 5/1999 | Estes et al. | 128/204.23 |
| 5,902,250 A | * 5/1999 | Verrier et al. | 600/515 |
| 5,904,141 A | * 5/1999 | Estes et al. | 128/204.23 |
| 5,928,133 A | * 7/1999 | Haljak | 600/26 |
| 5,953,713 A | * 9/1999 | Behbehani et al. | 706/16 |
| 5,970,975 A | * 10/1999 | Estes et al. | 128/204.23 |
| 6,000,396 A | * 12/1999 | Melker et al. | 128/204.21 |
| 6,029,665 A | * 2/2000 | Berthon-Jones | 128/204.23 |
| 6,049,730 A | * 4/2000 | Kristbjarnarson | 600/509 |
| 6,070,098 A | * 5/2000 | Moore-Ede et al. | 600/544 |
| 6,091,973 A | * 7/2000 | Colla et al. | 600/324 |

* cited by examiner

| state # | state | epoch n | epoch n+1 | epoch n+2 | epoch n+3 | epoch n+4 | epoch n+5 | epoch n+6 | epoch n+7 | epoch n+8 | epoch n+9 | epoch n+10 |
|---|---|---|---|---|---|---|---|---|---|---|---|
| S1 | hyp | Y | N | N | Y | N | N | N | N | N | N | N |
| S2 | apn | N | N | N | N | N | N | N | N | N | N | N |
| S3 | 3.mix | N | N | Y | N | N | N | N | N | N | N | N |
| S4 | 4.SA02 | Y | N | N | N | N | N | N | N | N | N | N |
| S5 | Obs | N | N | N | N | N | N | N | N | N | N | N |
| S6 | REM | N | N | N | N | N | N | N | N | N | N | N |
| S7 | arous | Y | N | N | Y | Y | Y | N | N | N | N | N |
| S8 | wake | Y | Y | Y | Y | Y | Y | N | N | N | N | N |
| S9 | stg 1 | N | N | N | N | N | N | Y | Y | Y | Y | Y |
| S10 | stg 2 | N | N | N | N | N | N | N | N | N | N | N |
| S11 | stg 3 | N | N | N | N | N | N | N | N | N | N | N |
| S12 | stg 4 | N | N | N | N | N | N | N | N | N | N | N |
| S13 | snore 0-low | | | | | | | | | | | |
| S14 | snore 1 med | | | | | | | | | | | |
| S15 | snore 2 high | | | | | | | | | | | |
| S16 | snore 3 v high | | | | | | | | | | | |
| S17 | heart rate 0-normal | | | | | | | | | | | |
| S18 | heart rate 1-high | | | | | | | | | | | |
| S19 | heart rate 2-low | | | | | | | | | | | |
| S20 | heart rate 3-arryth. | | | | | | | | | | | |

FIG 4

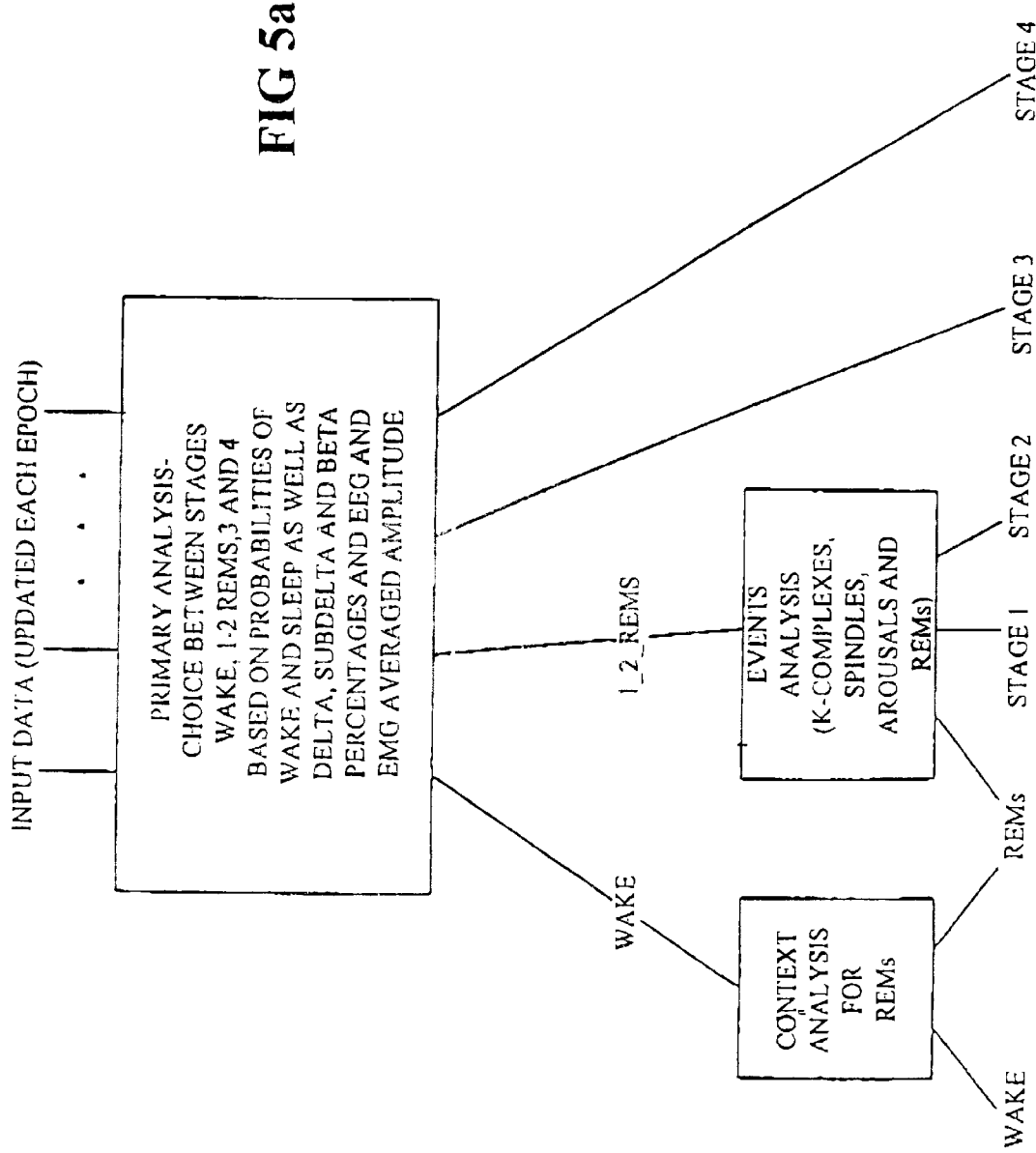

*1. after each 1 sec:*

```
CALCULATE
MAXIMUM AND MINIMUM
VALUES of
EEG WAVEFORM
```

```
STORE the PERIODS
and AMPLITUDES of the waves
which have PEAK to PEAK
more than (MAX-MIN)/4
```

```
CALCULATE
the TOTAL DURATIONS
and AVERAGE AMLITUDES
of
BETA+SIGMA, ALPHA, THETA
and DELTA bands
```

```
STORE the DURATION and
AVERAGE AMPLITUDE
for TWO DOMINANT TYPES
TYPE 1 - BETA+SIGMA
TYPE 2 - ALPHA
TYPE 3 - THETA
TYPE 4 - DELTA
```

*2. after each epoch (20/30 sec):*

COMMON ANALYSIS of 1 sec DATA:
a. detection of points where an EEG waveform type changes - the two dominant bands change
b. calculation of SLEEP and WAKE probabilities:
    Prob(WAKE) = the total duration of alpha when it is one of dominant types;
    Prob(SLEEP) = the total duration of theta when it is one of dominant types+
               the total duration of delta when it is one of dominant types;

| Patient State | Pat. Posn | 5 | 5.5 | 6 | 6.5 | 7 | 7.5 | 8 | 8.5 | 9 | 9.5 | 10 | 10.5 | 11 | 11.5 | 12 | 12.5 | 13 | 13.5 | 14 | 14.5 | 15 | 15.5 | 16 | 16.5 | 17 | 17.5 | 18 | Def Val cmH2O | Opt Val cmH2O |
|---|---|---|---|---|---|---|---|---|---|---|---|---|---|---|---|---|---|---|---|---|---|---|---|---|---|---|---|---|---|---|
| wake | B | | | | | | | | 20 | 4 | | | | | | | | | | | | | | | | | | | 8 | 8.5 |
| stage 1 | B | 0 | 0 | 0 | 0 | 0 | 0 | 0 | 5 | 20 | 3 | 3 | 0 | 0 | 0 | 0 | 0 | 0 | 0 | 0 | 0 | 0 | 0 | 0 | 0 | 0 | 0 | 0 | 9 | 8 |
| stage 2 | B | | | | | | | | | 7 | | | | | | | | | | | | | | | | | | | | |
| stage 3 | B | | | | | | | | | | | | | | | | | | | | | | | | | | | | | |
| stage 4 | B | | | | | | | | | | | | | | | | | | | | | | | | | | | | | |
| REM | B | | | | | | | | | | | | | | | | | | | | | | | | | | | | | |
| arousal | B | | | | | | | | | | | | | | | | | | | | | | | | | | | | | |
| microaro usal | B | | | | | | | | | | | | | | | | | | | | | | | | | | | | | |
| movement time | D | | | | | | | | | | | | | | | | | | | | | | | | | | | | | |
| wake | F | | | | | | | | | | | | | | | | | | | | | | | | | | | | | |
| stage 1 | F | | | | | | | | | | | | | | | | | | | | | | | | | | | | | |
| stage 2 | F | | | | | | | | | | | | | | | | | | | | | | | | | | | | | |
| stage 3 | F | | | | | | | | | | | | | | | | | | | | | | | | | | | | | |
| stage 4 | F | | | | | | | | | | | | | | | | | | | | | | | | | | | | | |
| REM | F | | | | | | | | | | | | | | | | | | | | | | | | | | | | | |
| arousal | F | | | | | | | | | | | | | | | | | | | | | | | | | | | | | |
| microaro usal | F | | | | | | | | | | | | | | | | | | | | | | | | | | | | | |
| movement time | F | | | | | | | | | | | | | | | | | | | | | | | | | | | | | |
| wake | L | | | | | | | | | | | | | | | | | | | | | | | | | | | | | |
| stage 1 | L | | | | | | | | | | | | | | | | | | | | | | | | | | | | | |
| stage 2 | L | | | | | | | | | | | | | | | | | | | | | | | | | | | | | |
| stage 3 | L | | | | | | | | | | | | | | | | | | | | | | | | | | | | | |
| stage 4 | L | | | | | | | | | | | | | | | | | | | | | | | | | | | | | |
| REM | L | | | | | | | | | | | | | | | | | | | | | | | | | | | | | |
| arousal | L | | | | | | | | | | | | | | | | | | | | | | | | | | | | | |
| microaro usal | L | | | | | | | | | | | | | | | | | | | | | | | | | | | | | |
| movement time | L | | | | | | | | | | | | | | | | | | | | | | | | | | | | | |

NUMBER OF OPTIMAL EPOCHS FOR EACH GAS DELIVERY PRESSURE

| States / events | EPOCHS NUMBERS | | | | | | | | |
|---|---|---|---|---|---|---|---|---|---|
| | 1 | 2 | 3 | 4 | 5 | 6 | 7 | 8 | 9 |
| Sleep state | Wake | Wake | Wake | Wake | Wake | Wake | Wake | Wake | Wake |
| Respiratory events | None | None | None | None | None | None | None | None | None |
| Arousal event | 3 | 2 | 1 | 2 | 3 | 5 | 4 | 2 | 0 |
| Patient position | S | S | S | S | S | S | S | S | S |

FIG 10

| States & events | \multicolumn{18}{c}{epoch numbers} |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| Sleep state | W | W | W | W | W | W | W | W | 1 | 1 | 1 | 2 | 2 | 2 | 2 | 2 | 2 | 2 |
| Respiratory event type | - | - | - | - | - | - | - | - | - | - | - | O | C | O | - | - | - | - |
| Arousal event and type | - | - | - | - | - | - | - | - | - | - | - | A | A | A | A | - | - | - |
| Patient position | S | S | S | S | S | S | S | B | B | B | B | L | L | L | L | L | L | L |
| Is patient state stable? Y/N | Y | Y | Y | Y | Y | Y | Y | Y | Y | Y | Y | N | N | N | Y | Y | Y | Y |
| Nominal pressure value-CMH20 | 8 | 8 | 8 | 8 | 8 | 8 | 8 | 8 | 8 | 8 | 8 | 9 | 9.5 | 10 | 10 | 10 | 10 | 10 |

TABLE KEY

| | |
|---|---|
| PATIENT LEFT POSITION | L |
| PATIENT RIGHT POSITION | R |
| PATIENT FRONT POSITION | F |
| PATIENT BACK POSITION | B |
| PATIENT SITTING POSITION | S |
| STAGE 1 SLEEP | 1 |
| STAGE 2 SLEEP | 2 |
| STAGE 3 SLEEP | 3 |
| STAGE 4 SLEEP | 4 |
| STAGE REM SLEEP | R |
| STAGE MOVEMENT TIME | M |
| AROUSAL | A |
| OBSTRUCTIVE SLEEP APNEA | O |
| MIXED APNEA | M |
| CENTRAL APNEA | C |

FIG 11

APPARATUS FOR GAS DELIVERY

The present invention relates to apparatus for controlling gas delivery to a patient. The apparatus may provide a diagnostic and/or a therapeutic function. The diagnostic function may include monitoring and/or diagnosis of physiological variables associated with the patient. The therapeutic function may include application of controlled gas delivery to the patient.

The apparatus of the present invention is particularly useful for investigation, diagnosis and treatment of sleep, respiratory and sleep related respiratory disorders, sleep propensity and fatigue and will be described herein in that context. Nevertheless it is to be appreciated that it is not thereby limited to such applications.

Sleep apnea syndrome is a respiratory disorder affecting between 4 and 5% of the population and is now well documented in a number of reputable medical journals. Sufferers of this debilitating disorder suffer reduced sleep efficiency, excessive blood pressure, cardiovascular effect ranging from mild to fatal, amongst other adverse health consequences and risks. It is recognised that an increase in upper airway resistance attributed to relaxation of upper airway muscles during sleep, contributes to cessation of breathing at frequent intervals during an Obstructive Sleep Apnea (OSA) patient's sleep. OSA is now relatively well documented and understood within the respiratory and sleep medical fields.

In the early 1980's a development commonly referred to as Continuous Positive Air Pressure (CPAP) was discovered as a front line cure for OSA (Sullivan). CPAP is a device which applies a continuous positive air pressure to the patient's airway by way of a nasal mask. This nasal mask is worn by the patient during sleep and a positive air pressure is applied to the patient's airway in order to keep the patients airway open and prevent a collapse of the patient's airway, which would otherwise lead to OSA.

Development of CPAP devices have been pursued by a range of manufacturers across the world and a number of variations of CPAP have also been introduced to the market place. These variations include, inter alia:

Demand Positive Air Pressure (DPAP) which is a device that supplies positive air pressure by detecting the patients respiratory cycle and applies the air pressure when the patient 'demands' this:

Bi positive air pressure (BIPAP), which is a device that allows two states of positive pressure and monitors the patient's respiration and delivers air pressure depending on whether the patient is undergoing inspiration or expiration; and Variable Positive Air Pressure (VPAP) which is a device that delivers a varying air pressure depending upon the patient's respiration cycle.

Other devices have been developed to automatically adjust air pressure delivered to a patient during sleep.

Whilst the prior art recognizes that respiratory disorders such as apnea or hypopnea may be addressed by applying positive air pressure to a patient, it has failed to recognize that even without the presence of respiratory events such as hypopnea or apnea (as detected or diagnosed by conventional means) upper airway resistance can exist and results in a reduction of a patient's sleep efficiency. The apparatus of the present invention may diagnose such upper airway resistance by detecting arousals. Arousals may be detected, for example, from a shift in frequency of the patients Electroencephalogram (EEG) and/or Electro-oculogram (EOG).

It is therefore recognised that even after treatment for OSA by application of the above mentioned CPAP or variations thereof, a patient can still experience arousals or micro-arousals during a night's sleep. These arousals and micro-arousals can be due in part to the fact that the air pressure required to be delivered to the patient to prevent OSA can vary depending upon the patients sleep position, sleep state and other factors such as intake of alcohol or drugs consumed prior to sleeping. The arousals and micro-arousals may be linked or associated with respiratory disorders.

It has been shown that many arousals or micro-arousals can occur during a patient's sleep. The present invention may provide apparatus for monitoring the patient's physiological variables and to diagnose corresponding physiological states including sleep, arousal and respiration events while at the same time controlling delivery of gas to a patient via a nasal or nasal and oral mask. The apparatus can in one mode be adapted to diagnose physiological states and in another mode adjust the pressure of air delivery to the patient to a level which accurately reflects the patient's state of wakefulness, sleep or arousal.

Due to the complex and varying states of sleep and broad range of sleep disorders that can be diagnosed, many different physiological variables (raw data) and events (derived data) may be monitored and/or analysed. While some positive air pressure devices exist which can monitor respiratory parameters, the present applicant is not aware of any prior art device which is able to monitor and diagnose a comprehensive range of both sleep and respiratory parameters. The monitored variables/events can include one or more of the following:

| | |
|---|---|
| Electroencephalogram | (EEG) |
| Electro-oculogram | (EOG) |
| Electro-myogram | (submental EMG from muscles under the chin) |
| Electro-myogram | (diaphragm EMG from respiratory effort |
| Electro-myogram | (other EMG reflecting muscle and nerve activity either by invasive or non-invasive monitoring) |
| Status of patient position | |
| Breathing and snoring sounds | (via microphone) |
| Leg movements | (Left and/or Right legs) |
| Electrocardiogram | (ECG) |
| Oximetry | ($S_2O_2$ - Oxygen saturation); |
| Carbon dioxide monitoring | $CO_2$ |
| Respiratory effort | (Abdominal, thoracic or otherwise) |
| Airflow | (Nasal or oral) |
| Continuous Positive Airflow Pressure | (monitoring of patients mask pressure during application of CPAP treatment) |
| CPAP mask temperature | (monitoring of CPAP mask air temperature for breathing activity and airflow of patient) |
| CPAP mask sound | (monitoring for patients breathing sounds within CPAP mask). These sounds include snoring, wheezing and other disordered breathing sounds |

Status of lights
Graphic processing of video image (allows determination of whether patients eyes are open or closed)

Patient digital video recording and graphic processing techniques for determination of eye lid activity (ie status of patient eyes being opened or closed—relative to fully closed or fully opened eyes status).

Time and date stamping of monitored physiological data, video and sound.

Infrared Video monitoring (for night studies)

Complex sound analysis (accurate full bandwidth or limited bandwidth recording and analysis of breathing sounds).

Physiological events: ie ECG arrhythmia, EEG spike detection, EEG spindles amongst others Endoscopy Breath by breath analysis-pnuemotachograph 3D imaging Infrared eye detection for fatigue and sleep monitoring EEG delta and alpha-wave detection Delta Wave detections and related sleep/fatigue/impairment detection Mattress Device: monitoring of patient sleep state and respiratory parameters by using a mattress sensor device. The matress device can be used to monitor a patient's electro-oculogram, sleep state, arousals, position, electrocardiogram. There are presently two types commercially available mattress devices; Static Charge-sensitive Bed (SCSB) and polyvinylidene fluoride (PVDF-piezoelectric plastic).

The apparatus of the present invention may monitor and diagnose a patient's EEG, EMG, EOG, position, breathing/snoring sounds and other variables/events while; at the same time control treatment such as positive air pressure. The positive air pressure treatment may be adjusted dynamically to suit the patients prevailing:

sleep state, respiratory events (ie OSA, central apnea, hypopnea, mixed apnea)

position (different air pressure may be required depending upon the patient's sleep position), arousals status (ie micro arousals may occur due to insufficient or excessive pressure), snoring (varying degrees of pressure may be required depending upon the patient's snoring—if for example the patient has taken alcohol or other drugs prior to their sleep, CPAP pressure may need to be varied in order to effectively eliminate snoring).

The apparatus of the present invention may deliver small or large adjustments in gas pressure delivery to the patient in order to maintain an appropriate pressure at all times.

The apparatus of the present invention may operate in one of several modes. The apparatus may operate in a diagnostic mode in which patient variables and/or events are monitored, processed and recorded for later review. Processing of the variables/events may be performed in any suitable manner and by any suitable means such as by means of a system as disclosed in AU Patent 632932 entitled "Analysis system for physiological variables". The diagnostic mode may include means for determining patient states. The latter may be derived from the monitored variables/events by means of one or more known automated sleep staging methodologies. The diagnostic mode includes means for determining an appropriate gas pressure setting for each patient state. The latter may be carried out by means of a pressure setting algorithm and stored in a look-up table for recall during the treatment mode.

The apparatus may operate in a treatment only mode wherein pressure settings determined during the diagnostic mode and stored in the look-up table may be applied to deliver gas to a patient according to the prevailing state of the patient as determined during the treatment mode.

The apparatus may operate in an integrated diagnostic and treatment mode wherein treatment via gas delivery is related to the currently monitored patient variables/events and diagnosed physiological states of the patient. The latter are determined in real time as part of the diagnostic mode.

A significant function of the diagnostic and integrated modes is to monitor the patient for micro-arousals. These micro-arousals can be detected from a change in frequency of the EEG and/or the EMG channels and/or by other means such as by detecting patient position/movement or by monitoring a mattress sensor device. By detecting the patient's micro-arousals, treatment of gas delivery can be correctly verified as providing an appropriate gas delivery for the patient. This method of arousal monitoring may determine whether or not the patient is actually being treated and benefiting from optimal sleep efficiency during gas delivery treatment.

The apparatus, includes means for monitoring one or more physiological variables including EEG, EOG, EMG, patient position and breathing/snoring. The monitoring means may include one or more transducers adapted to monitor the relevant physiological variable(s) such as a microphone for monitoring breathing/snoring sounds, and to provide an analog signal output indicative of the monitored variable. The monitoring means may include one or more electrodes applied to a part or parts of the body of the patient such as the skull, canthus, chin, legs etc. The monitoring means may also include means suitable for monitoring inter alia, oxygen saturation, $CO_2$ levels, respiratory effort, breathing and snoring sounds.

The apparatus includes means for analog processing the or each channel or signal obtained by the monitoring means. The analog processing means may include means for preamplifying conditioning and filtering the signal(s). The apparatus may include means for converting the processed signal(s) to a digital signal(s). The conversion may be carried out in any suitable manner and by any suitable means such as an analog to digital converter.

The apparatus includes means for processing the digital signal(s). The digital processing means may include a digital computer such a microprocessor or microcomputer. The digital processing means may be programmed via suitable software means to derive from the monitored physiological variables corresponding patient states and/or events. The processing means may make use of one or more algorithms to automatically derive the patient states and/or events.

The algorithm(s) may be adapted to derive, inter alia, hypopnea, obstructive apnea, central apnea and mixed apnea respiratory events, arterial oxygen desaturation ($SaO_2$), wake, arousal and REM sleep states, and stages 1, 2, 3 or 4 of sleep for each epoch. The number of epochs entered for each state may vary but should be sufficient to allow a measure of confidence for each patient state. For example, if there were only one epoch of REM sleep considered stable, this may prompt a clinician to review the patient's data as there may be a case for further investigation due to a below normal occurrence of REM sleep. A sequence of patient states for each epoch may be derived via this process. Where a large range and types of variables are being monitored, the processing means may be adapted to limit the number of patient states, or combination of states which may be recognised in order to simplify configuration options and system use. The states/combinations available may depend upon the end use of the apparatus eg. whether the apparatus is intended to be used as a routine clinical tool or a research device.

The apparatus may include means for determining an appropriate gas delivery pressure for each patient state and/or context of patient states or combinations thereof. The context may refer to a current combination of states or preceding states or combinations thereof. The pressure determining means may include means for increasing pressure in the event that a deterioration in respiratory event such as snoring, $S_aO_2$ desaturation, obstructive apnea, mixed apnea, central apnea, hypopnea or the like is detected. The pressure may continue to be increased until the event ceases, subject to a recommended maximum pressure not being exceeded. To more accurately establish a target pressure value wherein an increase in gas pressure ceases to cause improvement in effective breathing, it may be desirable to slightly overshoot the target value. Pressure may then be reduced upon detecting that a monitored event has deteriorated. The apparatus may also include means for detecting central apnea events triggered by the brain. In central apnea events gas delivery pressure changes may have little or no effect on a patient's respiratory function. It is therefore desirable to establish a central apnea condition before responding excessively to a respiratory event.

In one form the digital processing means may be programmed via suitable software to determine from each patient state and/or their contexts a gas pressure value beyond and below which there is a deterioration in a monitored event. The means for determining the appropriate gas delivery pressure may include a pressure seek algorithm. The algorithm may ensure that pressure to a patient is tracked up or down until it is appropriate for a prevailing event such as a stage of sleep. The algorithm may also ensure that the state of the patient is stable before recording a pressure value for the prevailing epoch. A table of pressure values for each patient state may be derived by this process. The table may indicate the number of epochs associated with a particular pressure value or values. It is expected that readings over several epochs will cluster around a narrow range of pressure values for each patient state.

The table may be stored in a memory associated with the processing means. The memory, may be on board the apparatus or it may be located remotely from the apparatus and connectable thereto via any suitable means such as a telecommunication line and modern. In one form the remote memory may include a portable carrier such as a magnetic or smart card.

A process of seeking an appropriate gas delivery pressure values may be commenced with a default or manually entered value for each patient state. Values may be entered manually by a physician either locally or remotely. Default values may be determined from clinical trials. The default and manually entered values may be entered in a table of default pressure values.

Where the apparatus is to be operated in an integrated diagnostic and treatment mode, pressure values which are determined by the pressure seek algorithm may be used to control in real time a gas delivery device via a suitable interface. The gas delivery device may comprise a CPAP device or other externally controllable gas or air flow delivery unit. The pressure values which are determined by the pressure seek algorithm may be entered in a pressure set look-up table and retained for future use.

Where the apparatus is to be operated in a treatment mode, the pressure values which are stored in the pressure set look-up table may be accessed following patient state determination. The values entered in the pressure set look-up table may be used to control directly a gas delivery device. During treatment mode, pressure values appropriate to each patient state determined during the integrated diagnostic mode may be used. This may enable direct treatment of a patient where pressure values appropriate to each patient state have previously been determined for that patient.

Where the apparatus is to be operated in a diagnostic mode, data representing patient states derived from the monitored physiological variables may be recorded for later recall and review.

According to one aspect of the present invention there is provided apparatus for controlling gas delivery to a patient, said delivery being adapted to maintain a physiological event such as effective respiratory function and/or absence of arousals, said apparatus including:

means for monitoring one or more physiological variables associated with said patient;

means for deriving from said one or more variables, data representing physiological states of said patient corresponding to the or each variable; and means for determining from said data for each physiological state, a gas pressure value beyond and below which there is a deterioration in said event.

According to a further aspect of the present invention there is provided a method for controlling gas delivery to a patient, said delivery being adapted to maintain a physiological event such as effective respiratory function and/or absence of arousals, said method including the steps of:

monitoring one or more physiological variables associated with said patient;

deriving from said one or more variables, data representing physiological states of said patient corresponding to the or each variable; and determining from said data for each physiological state, a gas pressure value beyond and below which there is a deterioration in said event.

A preferred embodiment of the present invention will now be described with reference to the accompanying drawings wherein:

FIG. 4 shows one form of a patient state table with 11 epoch examples;

FIGS. 5a and 5b show the general structure of one form of automatic sleep staging algorithm and an algorithm for evaluating probabilities of wake and sleep;

FIGS. 7a and 7b show one form of a pressure set look up table according to the present invention;

FIG. 8 shows one example of diagnostic monitoring modes according to the present invention;

FIG. 10 shows a simplified patient state table; and

FIG. 11 shows one form of default pressure table.

Figure 1:
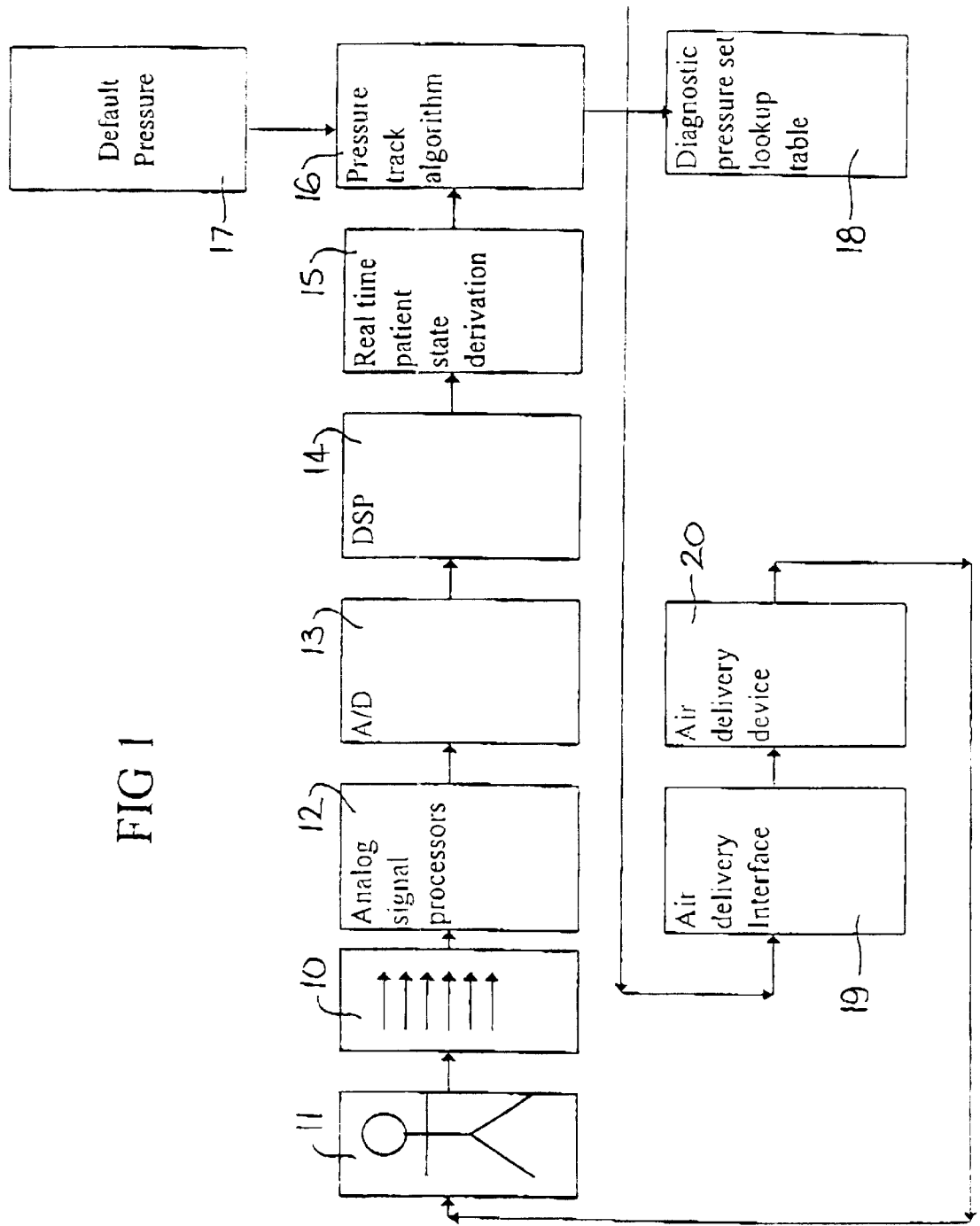
FIG. 1 shows a block diagram of apparatus according to one embodiment of the present invention.

Referring to FIG. 1, patient interface means 10 is adapted to monitor a plurality of physiological variables associated with a patient 11. Patient interface means 10 includes one or more electrodes and/or transducers adapted to monitor, inter alia, EEG, EMG, EOG, patient position and breathing to provide at their respective outputs analog signals indicative of the variables being monitored. A separate channel may be provided for each variable being monitored. The analog output signals of patient interface means 10 are inputted to analog signal processing means 12. Analog processing means 12 includes one or more signal amplifiers, filters etc. for preamplifying and preconditioning the signals to an appropriate bandwidth and amplitude level to provide a suitable input to analog to digital (A/D) converter means 13. A/D converter means 13 may include one or more A/D converters and is adapted to convert the analog processed signals to digital data. A/D converter means 13 may digitise each analog channel at a sampling rate suitable for that particular channel's signal and to a format which can be read by digital signal processing means 14. Digital processing means 14 includes a microprocessor or microcomputer and is adapted to accept digital data from A/D converter means 13.

Digital processing means 14 includes means 15 for deriving from the digital data, patient states/events corresponding to the monitored variables such as sleep stage 1, 2, 3, 4, PLM, arousal state, respiratory event, etc., during each epoch. Each epoch may be defined by a time segment having a set duration eg. 20 to 30 seconds. The patient state deriving means 15 may include an automatic sleep staging algorithm. After determining which channels of data are being presented (ie. which physiological variables are being monitored) the sleep staging algorithm may derive in real time the prevailing patient state and enter this in a patient state table. In deriving the prevailing patient state, means 15 may take into account both real time data from the physiological channels being monitored as well as the context of the data ie. the context of the prevailing patient state/event being evaluated with reference to preceding states.

Digital processing means 14 implements a pressure seek algorithm 16 to determine for a prevailing patient state and its context an appropriate gas pressure value for that prevailing state. The pressure seek algorithm 16 may include an iterative process to determine the appropriate pressure value. The process may include increasing pressure if a respiratory event such as snoring, $S_aO_2$ desaturation, obstructive apnea or hyponea is detected until the event ceases, thereby providing an effective improvement in breathing. Pressure may initially be increased from a clinically predetermined default value entered in default pressure table 17 or a value set by an attending physician. FIG. 11 shows one form of default pressure table. To more accurately determine an appropriate pressure value a slight increase in pressure may be applied after an event ceases. The pressure may then be reduced until the event ceases and stabilizes. The resultant pressure value may then be entered into a pressure set look-up table 18.

The process may be repeated over many epochs and the results stored in a memory such as look up table 18. The memory may include a remote device such as a magnetic carrier or smart card. Where the apparatus is being used in a diagnostic only mode, data stored in look up table 18 may be uses for future reference or in a treatment only mode. Where the apparatus is being used in an integrated diagnostic and treatment mode, the output from pressure seek algorithm 16 is used to control in real time air delivery interface 19 associated with air delivery device 20 such as a CPAP or other externally controlled gas or air flow delivery device.

Figure 2:
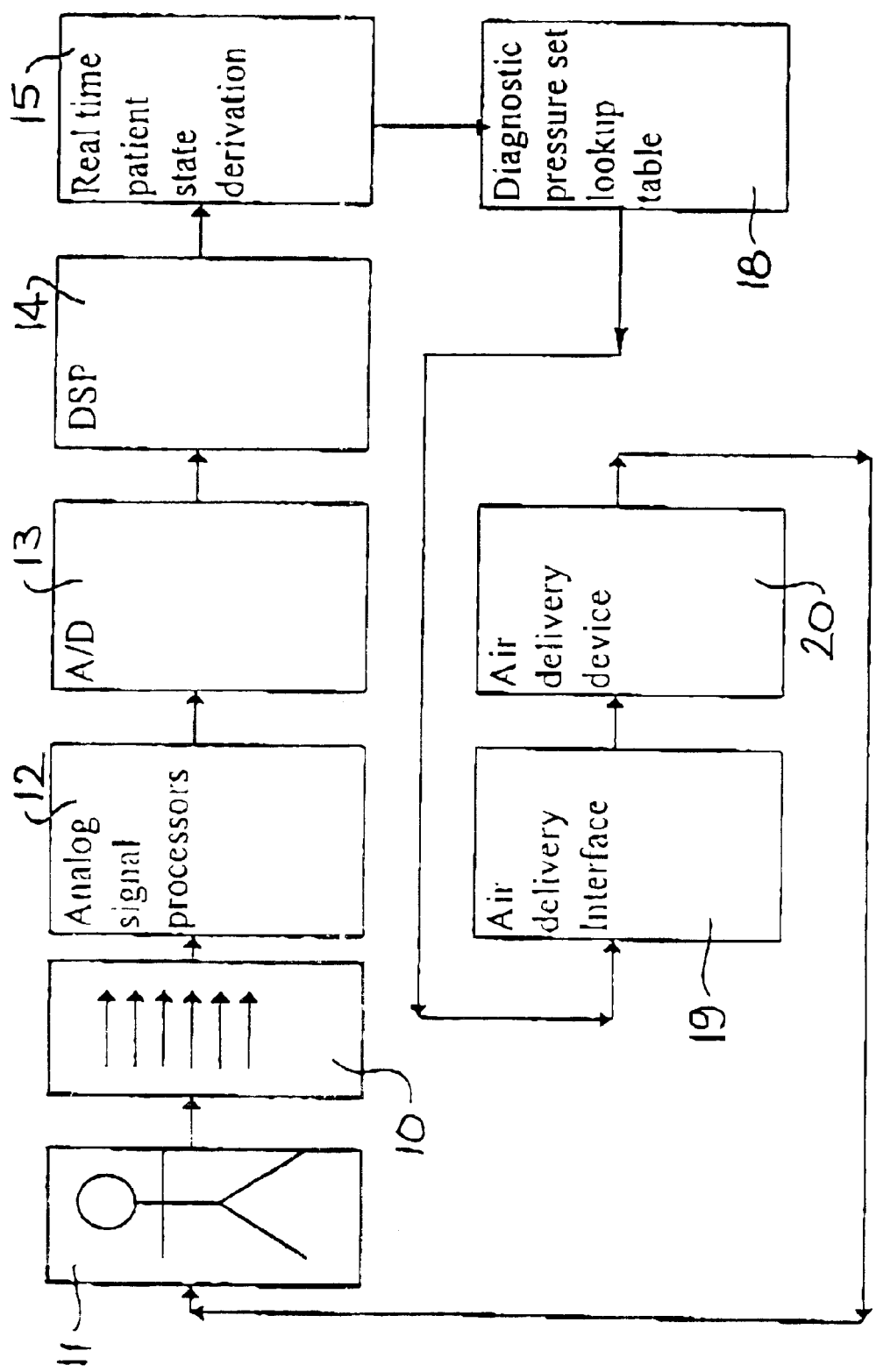
FIG. 2 shows a block diagram of the apparatus according to another embodiment of the present invention.

FIG. 2 shows the apparatus of FIG. 1 being used in a treatment mode. In FIG. 2 gas pressure values appropriate for each patient state are not determined in real time by pressure seek algorithm 16 but are instead read from pressure set look-up table 18, as determined and stored during a prior integrated diagnostic and treatment mode.

Figure 3A:
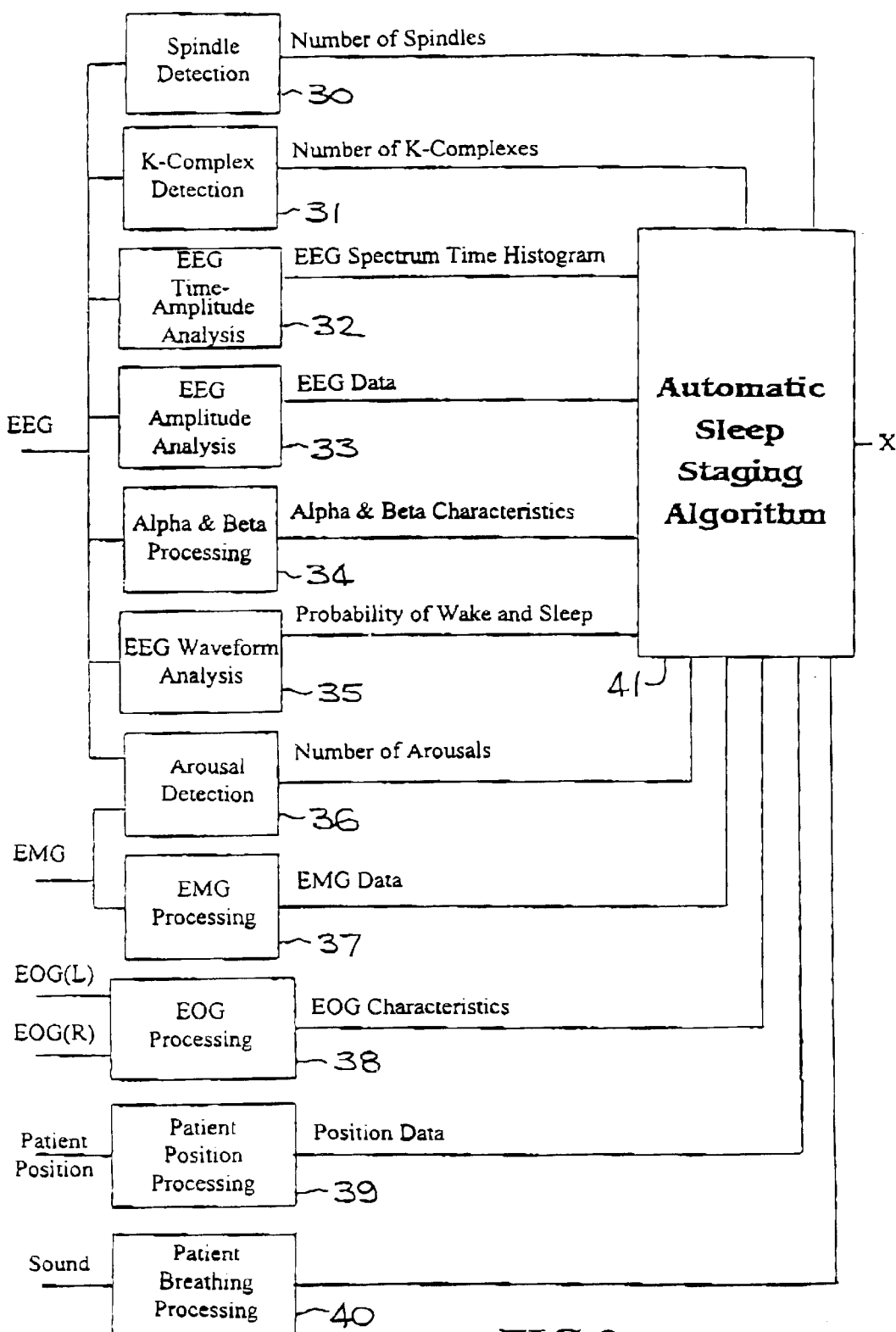
FIGS. 3a and 3b show a low chart of one form of patient state table determining algorithm according to the present invention.
Figure 3B:
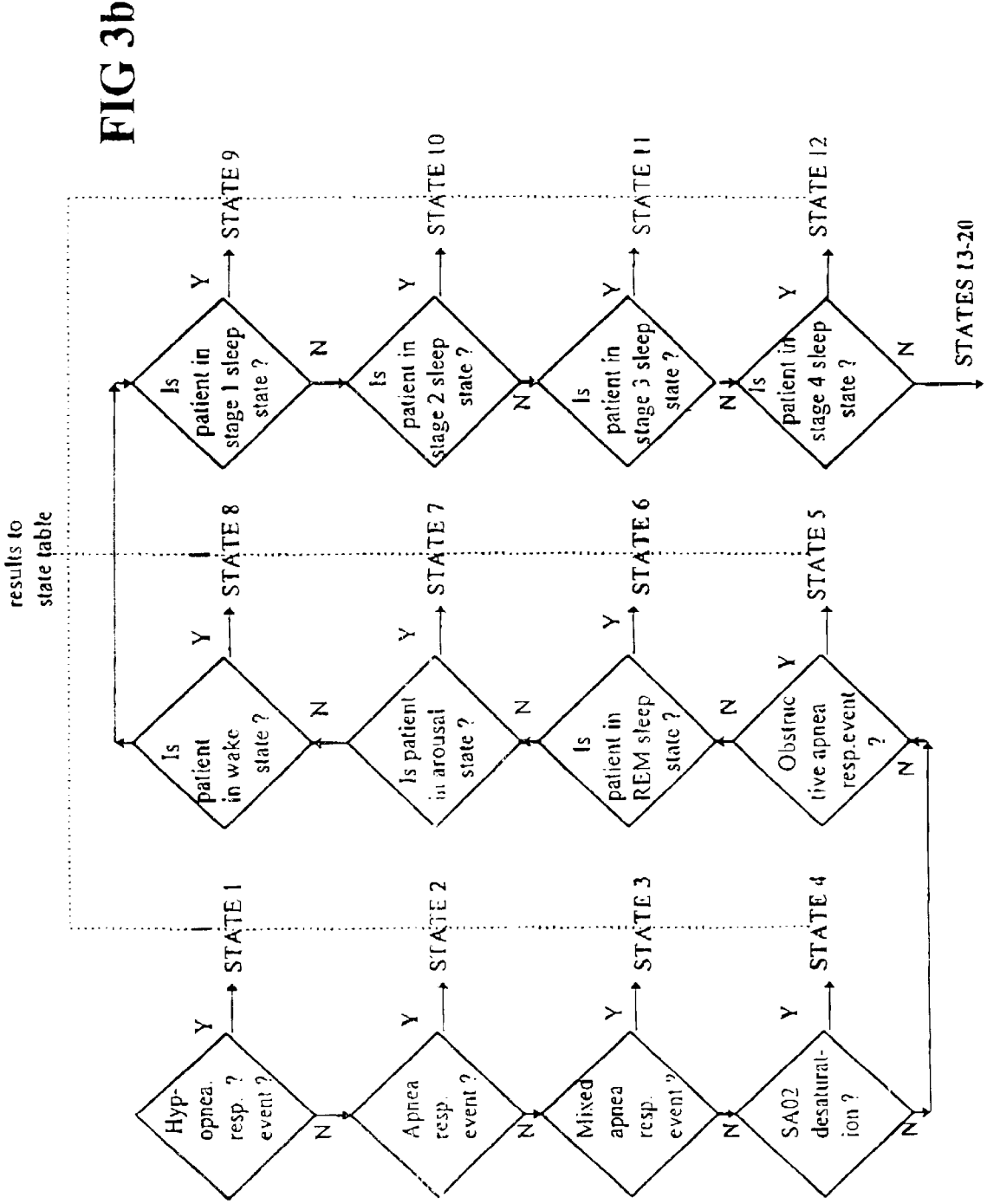

FIGS. 3a and 3b show a flow diagram of one form of patient state deriving means 15. Digital data representing EEG, EMG EOG and patient movement is inputted to modules 30 to 39. Modules 30 to 39 process the data to extract information required by sleep staging algorithm 41. The information processed includes an EEG histogram calculated using zero-crossing half-period analysis, "probabilities" of sleep and wake for the epoch (the "probability" of sleep in this context relates to delta and theta components), number of spindles, number of K-complexes, average EEG amplitude, relative average amplitude of EEG alpha, sigma and beta components (the purpose of this characteristic is to provide correct information about the high frequency EEG components when it is distorted by zero-crossing period amplitude analysis), number of arousals, average EMG amplitude, and REM analysis.

The output from sleep staging algorithm 41 is inputted to the patient state table determining algorithm shown in the flow chart of FIG. 3b. The outputs of the latter algorithm marked "STATE 1" to "STATE 20" are stored in a patient state table, an example of which is shown in FIG. 4.

FIGS. 5a and 5b show one form of automatic sleep staging algorithm 41. Such algorithms are known in the art and will not be described in detail herein. FIG. 5a shows the general structure of the sleep staging algorithm 41 and FIG. 5b shows a syntactic algorithm for evaluating probabilities of wake and sleep.

Figure 6A:
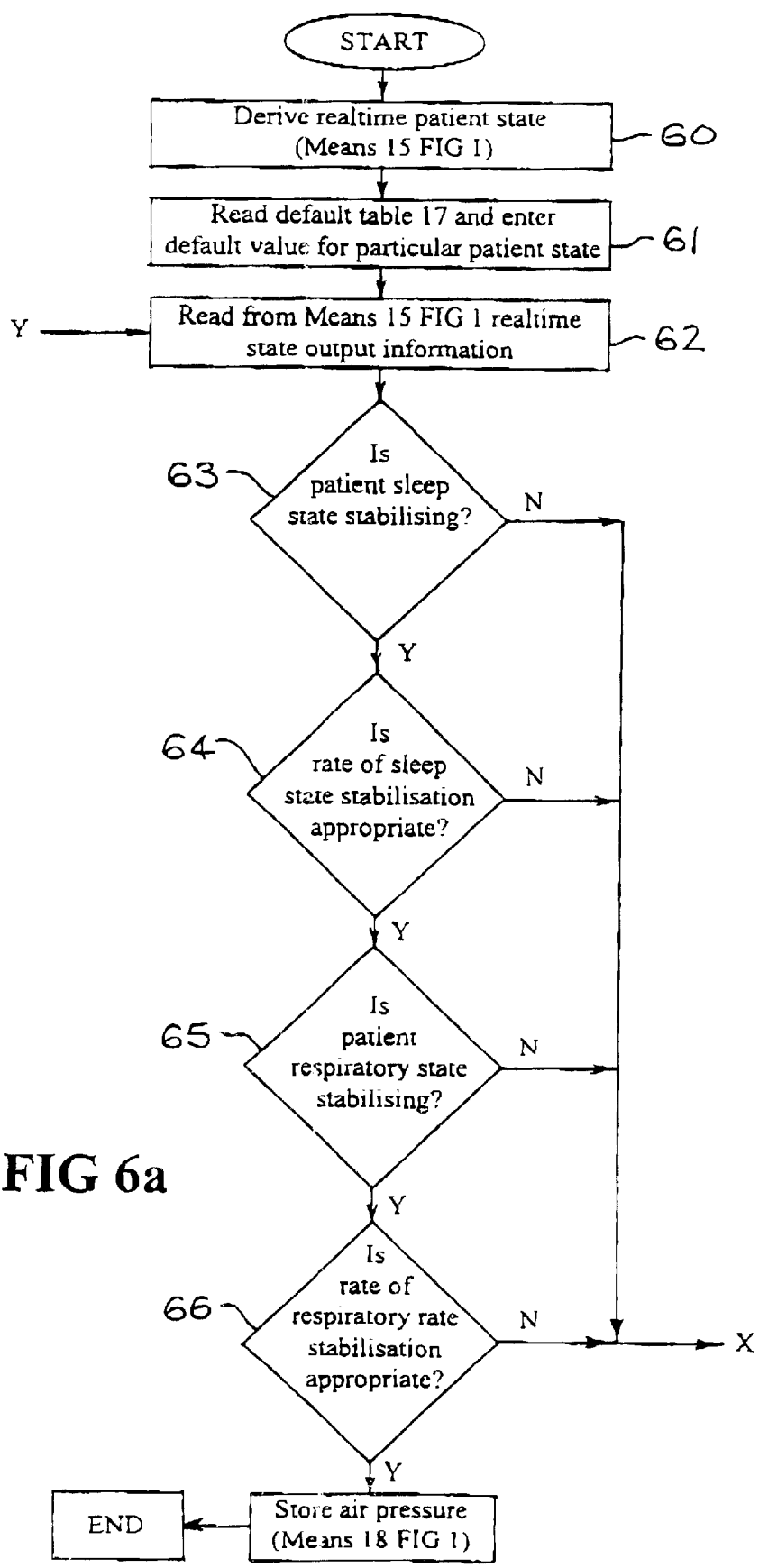
FIGS. 6a and 6b show a flow chart of one form of gas pressure seek algorithm according to the present invention.
Figure 6B:
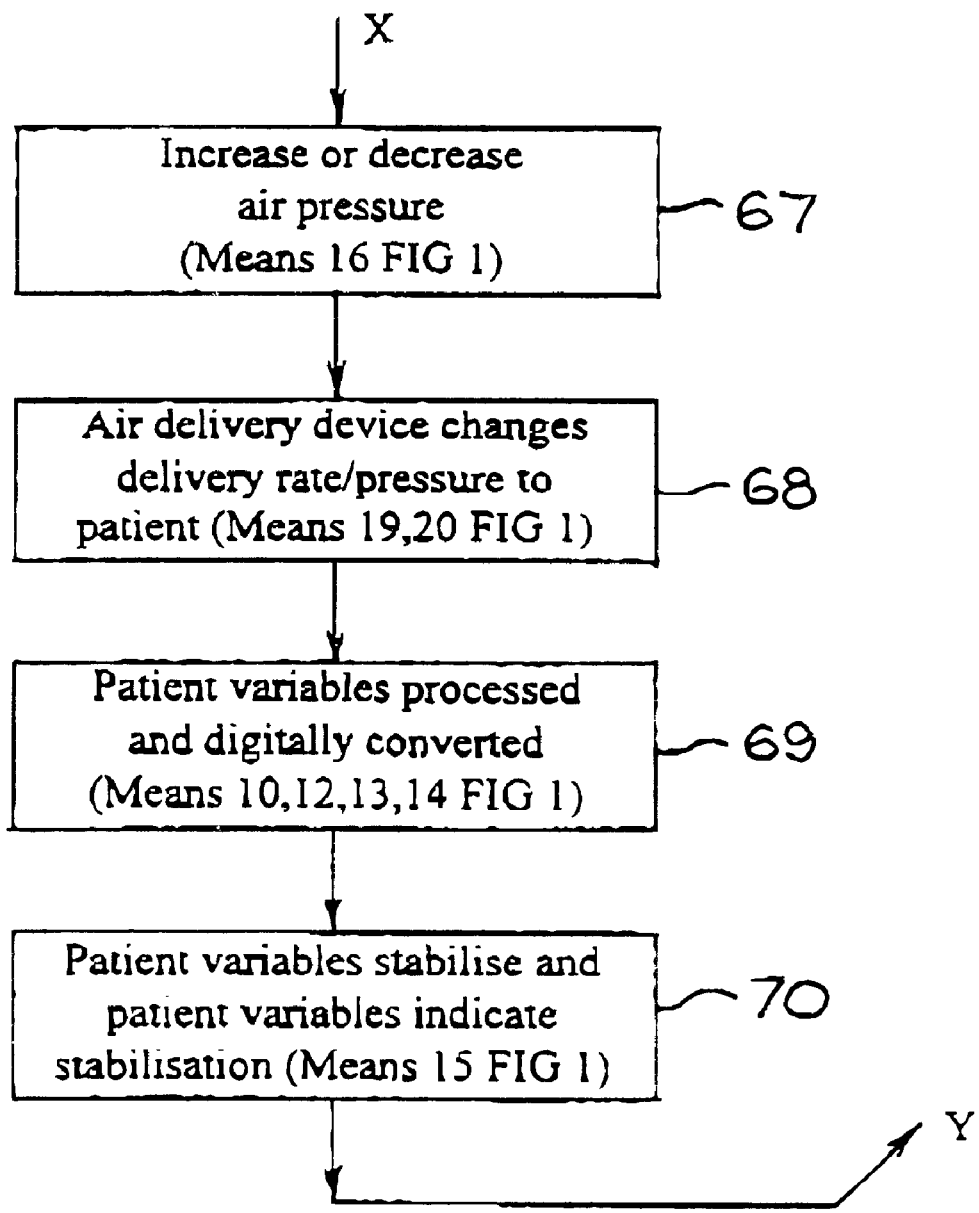

FIGS. 6a and 6b show a flow chart of an algorithm for determining appropriate gas pressure based on patient state. Real time patient state is derived at step 60 by patient state deriving means 15. Step 61 enters an initial pressure value for the particular patient state from default pressure table 17. Step 62 reads real time patient state information from patient state deriving means 15. Step 63 performs a test to establish whether the patient sleep state is stabilizing. This may be determined by events decreasing in frequency ie. by a reduction in occurrence of apneas, hypopneas, desaturations and/or arousals or by a patient's sleep state remaining constant or changing to a deeper stage of sleep, eg. stage 4 to REM, stage 1 to 2, stage 2 to 3, stage 3 to 4 and accompanied by a reduction in movement time. If the determination is no (N) pressure is increased or decreased (steps 67–68), the patient variables are reprocessed (step 69) and the algorithm returns to steps 62 and 63. If the determination is yes (Y), step 64 performs a test to establish whether the rate of sleep state stabilization, is appropriate. The latter is appropriate if it is occurring at a rate determined by clinical trials. If the determination is no (N) pressure is increased or decreased (steps 67–68), the patient variables are reprocessed (step 69) and the algorithm returns to steps 62 to 64. If the determination is yes (Y), step 65 performs a test to establish whether the patient respiratory state is stabilizing. As noted above this may be determined by events decreasing in frequency. If the determination is no (N) pressure is increased or decreased (steps 67–68), the patient variables are reprocessed (step 69) and the algorithm returns to steps 62–65. If the determination is yes (Y) step 66 performs a test to establish whether the rate of respiratory stabilization is appropriate. The latter is appropriate if the reduction in frequency or severity of the respiratory event is occurring at a rate determined by clinical trials. If the determination is no (N) pressure is increased or decreased (steps 67–68), the patient variables are reprocessed (step 69) and the algorithm returns to steps 63 to 66. If the determination is yes (Y) the air pressure is stored in pressure set look-up table 18.

Figure 7B:
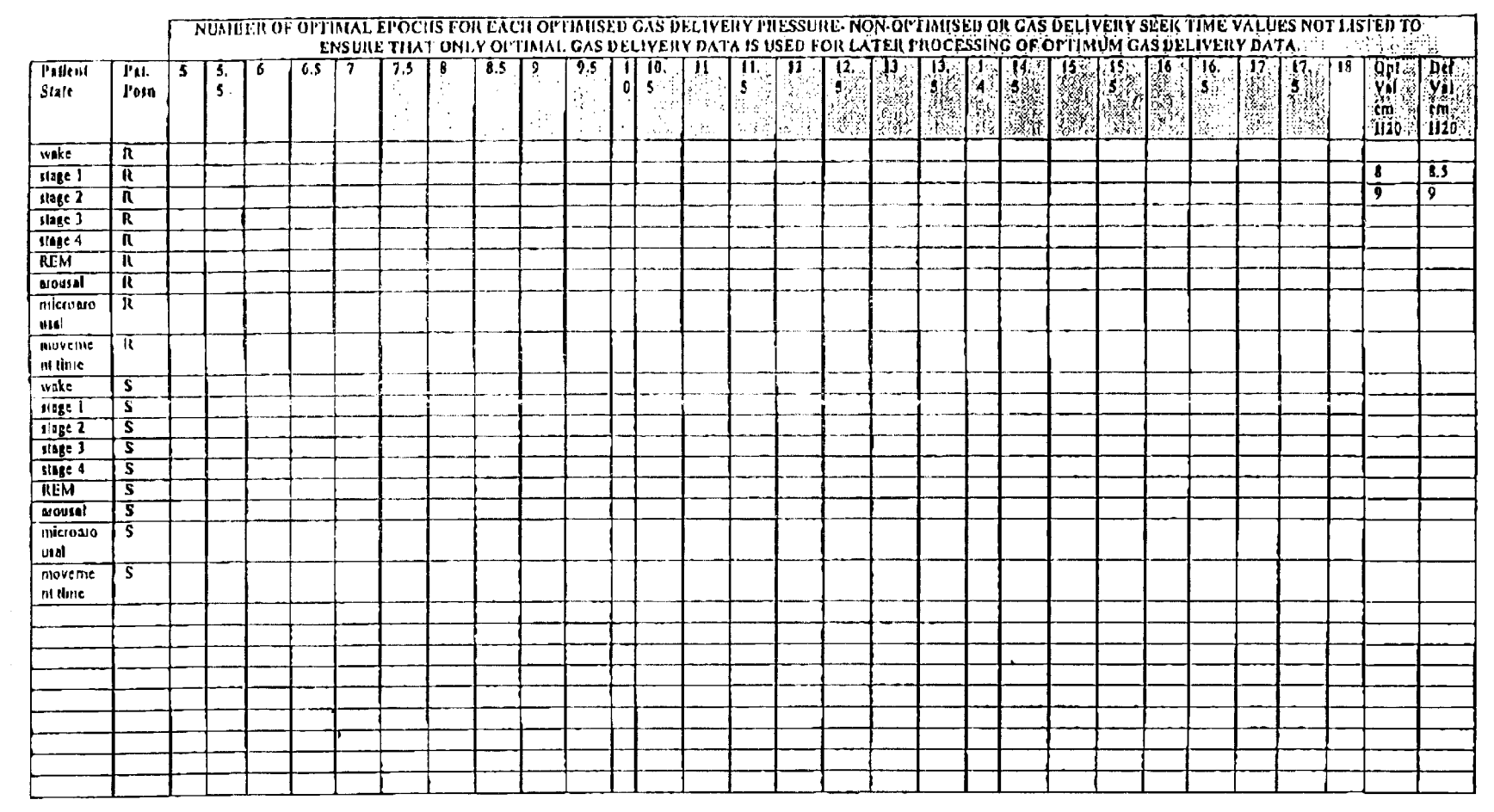

FIGS. 7a and 7b show one example of a pressure set look-up table. The numbers at the top of the table represent the epochs (each epoch is selectable to a 20 or 30 second time period) for each specific state and gas delivery. A table similar to FIGS. 7a and 7b can be created for each and every diagnostic study. Stages 1, 2, 3, 4 and REM may be listed where the patient state is considered stable, eg. the incidence of respiratory events, arousals and micro-arousals are at a minimum that can be archived with optimal pressure (achieved by tracking above and below what is considered-as optimal). Arousal, micro-arousal, wake and movement time are listed because the patient may wake, arouse or move due to external factors such as noise disturbance. The apparatus may apply an air pressure during these incidences which is most compatible with such an occurrence. This pressure may, for example, be an optimal pressure for stage 1, which most closely represents pressure in preparation for the first stage of sleep.

The pressure seek algorithm may ensure that pressure to the patient is tracked up and down and that the patient state is stable before the pressure value is noted into a particular epoch. A list of epochs where the pressure is considered "non-stable" may also be noted to allow validation and reply of the patient's diagnostic study for verification of data recorded during diagnostic operation of the apparatus.

The numbers of epochs entered for each state allow a measure of confidence for each patient state. If for example, there were only one epoch of REM sleep considered stable, this may prompt the clinician to review the patient's data as there may be a case for further investigation due to a below normal occurrence of REM sleep.

The table of FIGS. 7a and 7b represents the diagnostic output for a study but this table could be substituted for a single column of optimum pressure reading against each patient state. Alternatively the patient may be "calibrated" for different of types of study such as when the patient has had alcohol or other drug treatment. In these cases the patient may configure the apparatus to represent their condition from a range of options which may be calibrated for a particular patient. After sufficient clinical data is available it may be possible to extrapolate various conditions or other tables of pressure values from the patient's standard data, rather then having to conduct separate studies when the patient has had drugs administered or is excessively tired or is under the influence of other causes that could significantly affect the patient's gas delivery requirements.

The last columns of FIG. 7a and 7b show an example of default pressure settings. These default settings may be preset in the apparatus or determined by a supervising medical practitioner or healthcare worker.

Only the first two rows of the table have been filled in to serve as an example of the format of table. The default table may consist of a left hand state column plus several options of defaults depending on patient category—eg. severe apnea suspect etc.

In FIG. 7a it is apparent that during stage 1 sleep a pressure setting equal to 8.5 cm $H_2O$ was recorded during 20 epochs whilst the patient was on his back (B) and during stage 2 sleep a pressure setting equal to 9 cm $H_2O$ was recorded during 20 epochs. These are the appropriate pressure values for stages 1, 2 when the patient is lying on his back. Therefore these values are shown entered in the column marked opt val (optimum value). These are also the values which will be recalled in a treatment only mode.

Figure 8:
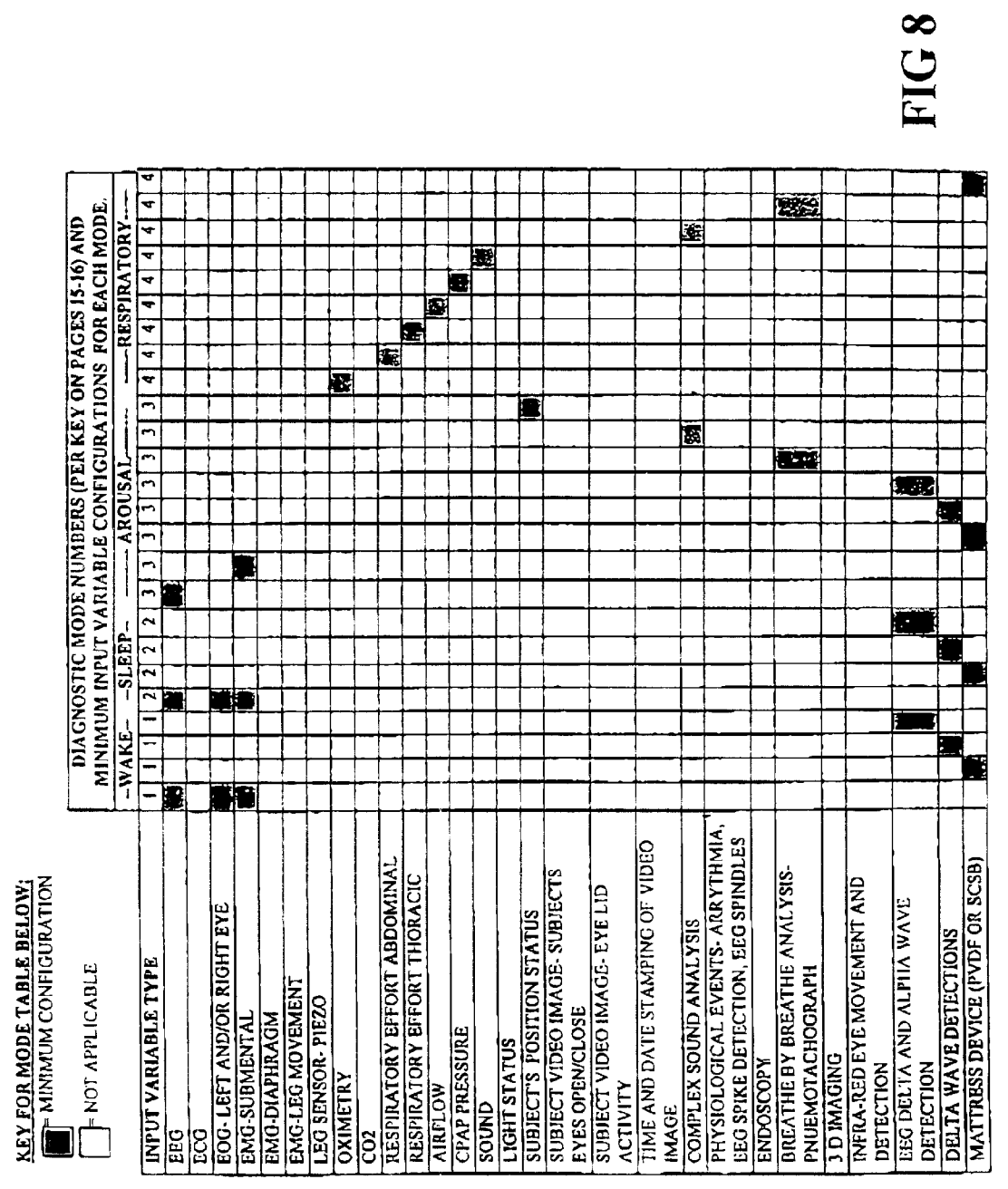

FIG. 8 shows a chart of some combinations of monitoring modes that may be made available to an end-user to simplify system use and configuration options. The modes available will depend on whether the present invention device is to be used as a routine clinical tool or a research device. Other factors that may determine what modes are available to end user include marketing factors—ie what the market requires in terms of end user options. The chart shows the optional minimum configurations for the various modes (1 to 16).

The key to monitoring modes 1–16 is as follows:

Mode Key Function

| | | |
|---|---|---|
| 1 | W- | represents wake state monitoring |
| 2 | S- | represents sleep state monitoring |
| 3 | A- | represents arousal state monitoring |
| 4 | R- | represents respiratory state monitoring |
| 5 | WS- | represents wake and sleep state monitoring |
| 6 | WA- | represents wake and arousal state monitoring |
| 7 | WR- | represents wake and respiratory state monitoring |
| 8 | SW- | represents sleep and wake state monitoring |
| 9 | SA- | represents sleep and arousal state monitoring |
| 10 | SR- | represents sleep and respiratory state monitoring |
| 11 | AS- | represents arousal and sleep state monitoring |
| 12 | AR- | represents arousal and respiratory state monitoring |
| 13 | WSA | represents wake, sleep and arousal state monitoring |
| 14 | WSR | represents wake, sleep and respiratory state monitoring |
| 16 | WSAR | represents wake, sleep, arousal and respiratory state monitoring |

For modes 5 to 16 the wake, sleep, arousal and respiratory modes can be combined according to the mode type, eg. WR (mode 7) means that the configuration for wake and respiratory are combined. The above modes are minimal configurations only and numerous other combinations are available. For example the respiratory mode shows a single channel being used for each mode illustrated but in fact any combination of the channels marked under respiratory mode can be used for the respiratory mode.

Figure 9A:
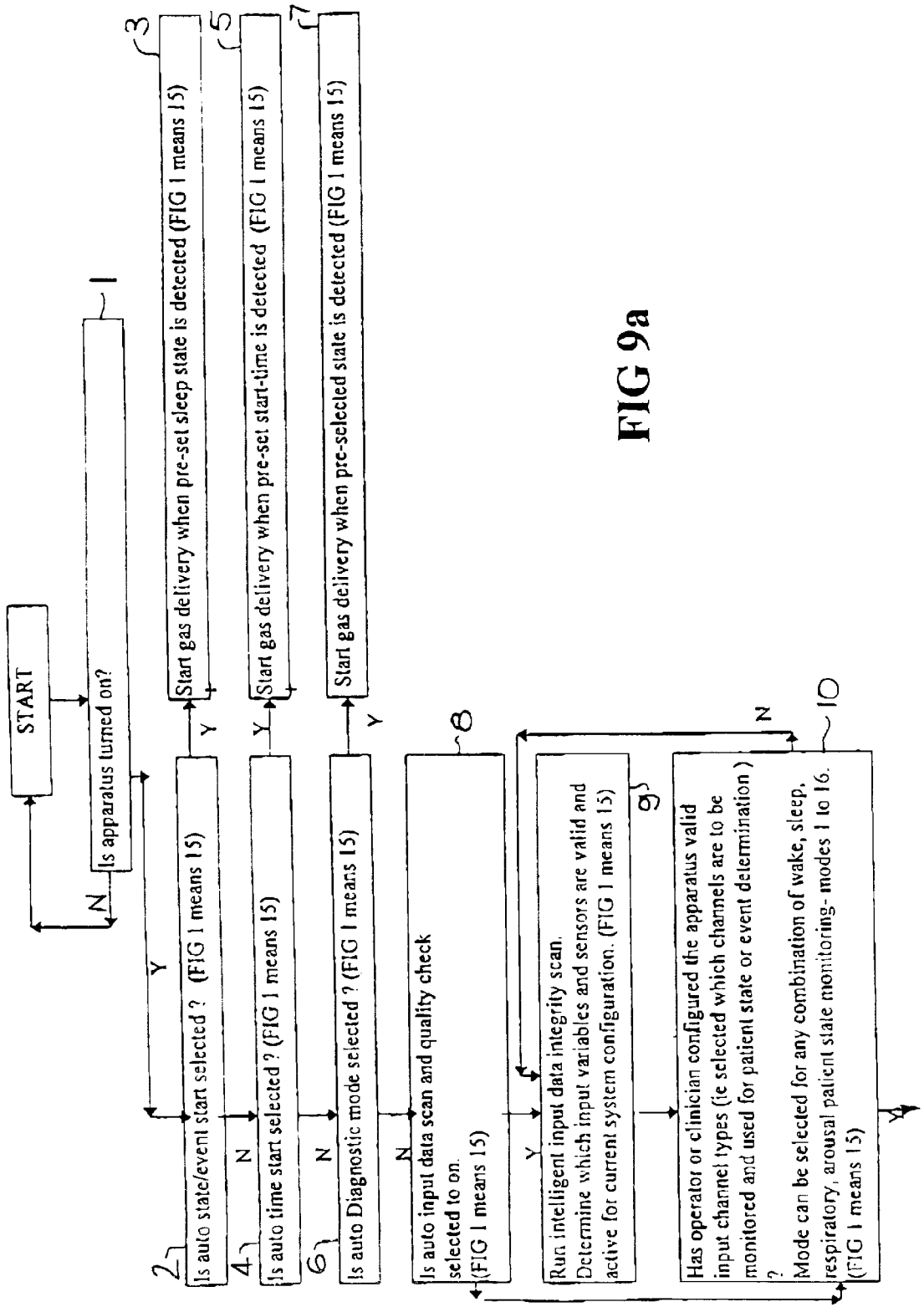
FIGS. 9a and 9b show a flow chart of another form of gas pressure seek algorithm according to the present invention.
Figure 9A:
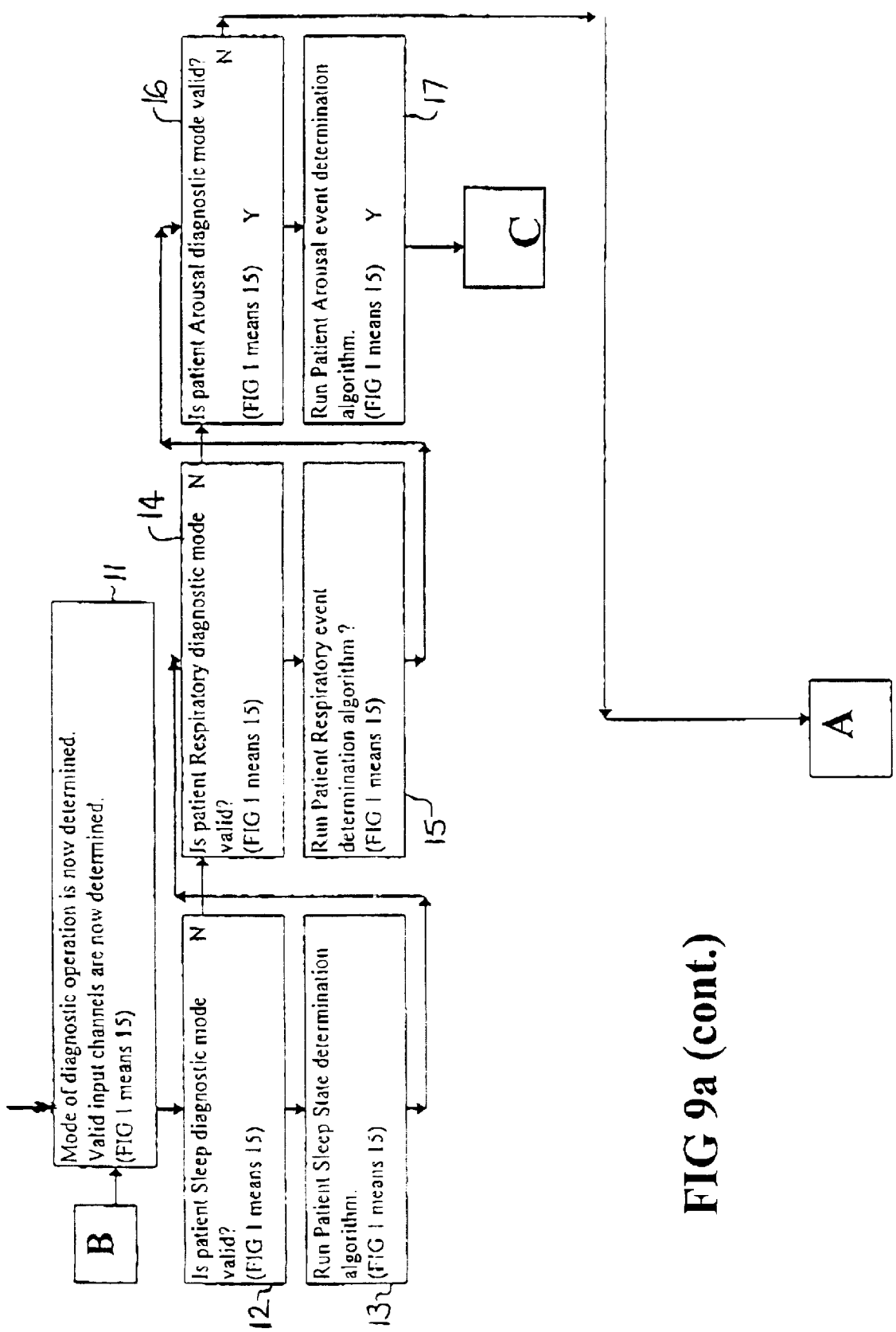
Figure 9B:
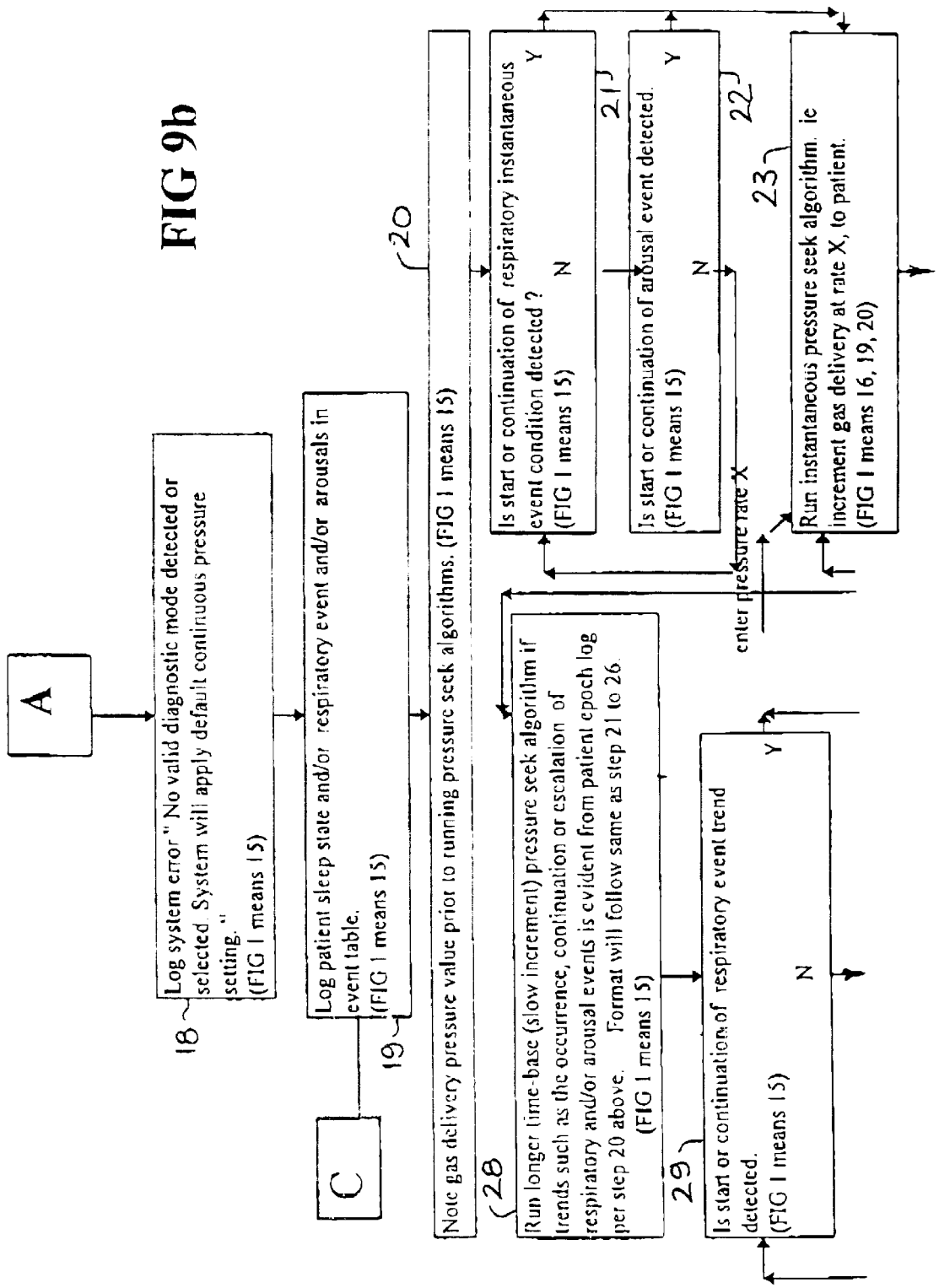
Figure 9B:
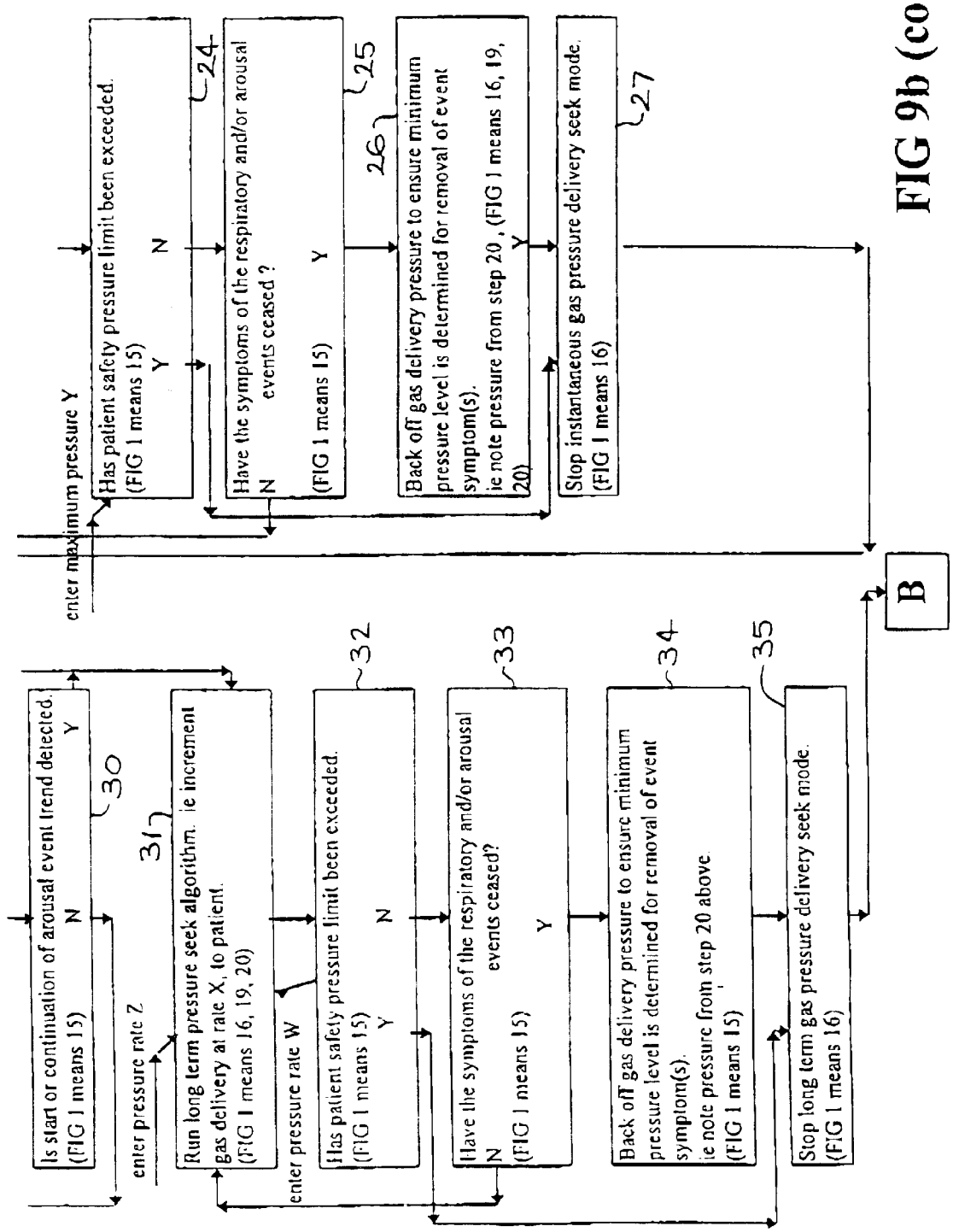

FIGS. 9a and 9b show a flow chart of a gas pressure seek algorithm with added refinements. Steps 1 to 35 of the flow chart are described below.

STEP 1

"Turned on" refers to apparatus being in active mode. This does not necessarily mean that the apparatus is operating a gas delivery mode but at least is in a standby or power on-mode ready for a clinician or patient to select start.

STEP 2

Auto event/state start may be selected to avoid patient discomfort during gas delivery, eg. when the patient is not yet in a sleep state or when the patient is not in a sleep state and requires gas delivery due to occurrence of a respiratory event.

STEP 3

After start is selected the apparatus will:

a) immediately start gas delivery to patient, or b) start gas delivery to patient when a pre-configured sleep state(s) is detected, or;

c) start gas delivery to patient when a pre-configured respiratory event(s) is detected, or;

d) start gas delivery to patient when a preconfigured arousal type(s) is detected, or;

e) start gas delivery to patient when a pre-configured periodic leg movement is detected.

STEP 4

Auto time start allows the apparatus to be switched on to gas delivery at a certain presented time. Auto-start may be selected concurrently with auto sleep/event start and the apparatus will start gas delivery after a set time and when a set state is detected.

STEP 5

The apparatus provides a means for automatically scanning physiological input variables from a patient and determines;
- a) whether the data is typical and accurate;
- b) whether the data is affected by some form of artefact or other distortion and alerts the system user or operator;
- c) what the artefact or other distortion is, and if possible automatically compensates for the artefact or distortion, eg. by way of filtering or gain change, switching to backup or secondary electrodes or sensors or by other means.

STEP 6

This step refers to applying an automatic channel integrity scan and determining which channels are valid and then using valid channel combinations to determine a valid diagnostic mode selection.

This automatic diagnostic mode selection can also be set for continuous update so that valid channels are reviewed during the patient diagnostic mode. The valid diagnostic mode can be reviewed to ensure that any channels that have dropped out or are no longer valid can be compensated for by an appropriate diagnostic mode (refer to FIG. 8 for a table of appropriate diagnostic modes). The diagnostic mode will be selected by determining valid input channels and then selecting a mode that has at least the minimum valid channels as listed in the diagnostic mode table.

If the operator selects only airflow from the mask feed as a means of patient data input and the automatic Diagnostic mode is selected, the apparatus will scan the input data if auto input data scar is selected and determine that the airflow mask channel is valid and will automatically select the diagnostic Respiratory event detection and possibly arousal detection only. Arousal may be deduced by determining an artefact signal riding on the airflow waveform.

STEP 7

Start gas delivery when pre-selected state is detected.

STEP 8

This mode can be selected on for start of a study only to determine valid channels or for "study mode on" where the input data will be scanned during study to ensure that input channels remain valid.

This can be achieved by selecting a mode type (ie selecting one of the configurations for combination of sleep, wake, respiratory or arousal monitoring—refer FIG. 8). By selecting one of the mode types the apparatus will indicate which parameters for the particular mode are required to be monitored from the patient.

Alternatively, a user can select channels that are required to be monitored and the apparatus may then automatically decide which diagnostic mode should be operated.

STEP 9

Input data integrity scan is a function which allows the input channels to be scanned for the purpose of determining whether the signal characteristics of these input channels are appropriate to indicate that the patient data is of suitable quality for further diagnostic processing.

For example the EEG, EOG and EMG electrodes can be scanned and analysed with reference to signal to noise ratio, frequency and amplitude characteristics in order to ensure that these parameters are within a normal range for a useable patient data channel. If, for example, the signal to noise ratio is excessively high for a particular channel or the frequency component of a channel consists of mains electro magnetic frequency, then this channel is likely to be either not connected or have a poor connection to the subject under diagnosis. It is therefore better to not use this patient data channel rather than risk inferior diagnosis of the patient Another means of scanning patient input data for verification of signal quality may be to evoke an impedance checking function. The impedance checking function may inject a small, safe, current through the patient's electrodes and if the patient electrode contact is poor then the current will produce a higher voltage indicating that the patient electrode may be in poor contact.

This type of input channel verification is normally evoked automatically by the apparatus, during a patient's use thereof. In this way signal integrity and subsequent gas delivery control is able to be continually verified for accuracy against patient variables. It is quite common for electrodes and sensors to come loose or develop poor connections during the night, while a patient is being monitored. It is desirable that the apparatus is able to compensate for this factor and to have sufficient intelligence not to incorrectly diagnose a patient through corrupt data from poor patient connections.

Another function of this step is to determine which patient channels are to be used for patient state derivation. The apparatus can in some embodiments be configured with as little as one channel of data being input. This channel could be an airflow channel, for example, as determined by sensing an airflow path provided by a gas delivery device to a patient.

The apparatus may use conventional pnuemotachograph data analysis and representation for monitoring patient's airflow and respiratory disorders or events.

This step can be run automatically during study in order to verify quality of input signals and if necessary diagnostic mode can be automatically changed to compensate for patient data channels which may not be of suitable quality to achieve accurate and reliable patient diagnostic treatment.

STEP 10

Valid input channels can be selected by the system user. Alternatively valid input channels can be automatically detected by the apparatus in step 7. The apparatus will dynamically scan and update the valid mode in accordance with scanned valid channels.

STEP 11

This step notes valid channel types and the subsequent valid mode for patient state and event determination. This information may be used in later stages of patient diagnostic state and event determination.

STEP 12

Valid Sleep Determination mode may be activated if the operator of the apparatus has selected this mode or if the automatic mode select function is activated at step 6 and input data scan detects at least the minimum configuration of input channels for sleep diagnostic mode.

STEP 13

If the Sleep diagnostic mode is activated the sleep state determination algorithm may be activated.

STEP 14

Valid Respiratory Determination mode may be activated if the operator of the apparatus has selected this mode or if the automatic mode select function is activated in step 6 and input data scan detects at least a minimum configuration of input channels for Respiratory diagnostic mode.

STEP 15

If the Respiratory diagnostic mode is activated a respiratory event determination algorithm may be activated.

STEP 16

Valid Arousal Determination mode may be activated if an operator of the apparatus has selected this mode or if the automatic mode select function is activated at step 6 and input data scan detects at least a minimum configuration of input channels for the Arousal diagnostic mode.

STEP 17

If the arousal diagnostic mode is activated an arousal state determination algorithm may be activated.

STEP 18

It is unlikely that the apparatus will not detect a valid mode as even the patient mask application allows the system to determine that the airflow sensor or the mask pressure sensor is a valid signal. In the case of a mask airflow signal only, for example, the apparatus may operate in a respiratory diagnostic mode.

One case where a valid diagnostic mode may not be detected is when the apparatus is turned on and the mask is not connected. In this case the airflow signal may be scanned and determined as invalid, in which case a continuous pressure may be applied to the mask until automatic signal validation determines that the airflow signal becomes valid when the patient applies the mask.

A default pressure applied to the patient's mask may be determined either by an attending physician or clinical data.

STEP 19

FIG. 10 shows a simplified table logging patient sleep state, respiratory event and arousal event for the first 10 epochs of a diagnostic mode operation.

STEP 20

The pressure value is noted before any seek routines are implemented so that a pressure value can be returned to in case, for example, the seek routine does not affect the patient respiratory or arousal events.

STEP 21

Is start or continuation of respiratory instantaneous event detected? Refer FIG. 1 means 15

STEP 22

Is start or continuation of arousal event detected?

STEP 23

Run instantaneous pressure seek algorithm, ie increment gas delivery at rate X, to patient. Enter pressure value X for determination of the rate of increase for pressure seek adjustment. The value of X may be determined from clinical studies which may be established to determine an effective value of pressure rate change for the purpose of optimising the patient's state.

STEP 24

Has patient safety pressure limit been exceeded?

Value Y represents a maximum pressure that can be applied to a patient. This value may be determined individually for different patients or may be a common value for a number of patients. Clinical trials may assist in determination of this value.

STEP 25

Are symptoms of the start or continuation of respiratory and/or arousal events being reduced?

The patient data needs to be continually monitored during pressure seek control to ensure that pressure changes assist in ceasing respiratory and/or arousal events.

STEP 26

Back off gas delivery pressure to a minimum pressure level required to avoid event symptom(s), ie. note pressure from step 20. This step ensures that excessive pressure is not supplied to the patient but rather that a minimum value of pressure is applied to stabilise the patient's state.

STEP 27

Stop instantaneous gas delivery pressure seek mode. This step prevents an increase in pressure where the pressure has corrected the arousal or respiratory event or a recommended maximum pressure is exceeded.

STEP 28

Longer term seek algorithms are required to determine whether a patient sleep can be improved by optmising patient gas delivery.

Some diagnostic evaluations conducted by means 15 (FIG. 1) in order to determine "appropriate" longer term pressure changes include:

a) is patient sleep state remaining constant or changing to deeper stage of sleep, eg. stage 4 to REM, stage 1 to 2, stage 2 to 3, stage 3 to 4, reduction in movement time, b) "appropriate" denotes that the rate that the rate at which sleep stages change into a deeper stage of sleep occur at an ideal rate, where the ideal rate may be determined by clinical trials;

c) "appropriate" also denotes that the reduction in frequency or severity of the respiratory event is occurring at an ideal rate, where the ideal rate may be determined by clinical trials;

d) determination of patient state stabilising including detection of:
events decreasing in frequency ie reduction in occurrence of apneas, hypopneas, desaturations and/or arousals.

STEP 29

Is start or continuation of respiratory event trend detected? Refer FIG. 1 means 15

STEP 30

Is start or continuation of arousal event trend detected?

STEP 31

Run long term pressure seek algorithm, ie. increment gas delivery at rate Z, to patient. Enter pressure value Z for determination of rate of increase for pressure seek adjustment. The value of Z may be determined from clinical studies which may be established to determine an effective value of pressure rate change for the purpose of optimising the patient's state.

STEP 32

Has patient safety pressure limit bee exceeded?

Value W represents a maximum pressure that can be supplied to the patient. This value may be determined individually for different patients or may be a common value for a number of patients. Clinical trials may assist in determining this value.

STEP 33

Are symptoms of start or continuation of respiratory and/or arousal events trend being reduced?

The patient data needs to be continually monitored during pressure seek control to ensure that pressure changes assist in ceasing respiratory and/or arousal events.

STEP 34

Back off gas delivery pressure to ensure that a minimum pressure level is determined to avoid event symptom(s), ie. note pressure from step 20. This step ensures that excessive pressure is not supplied to the patient but rather that a minimum value of pressure is applied to stabilise the patient's state.

STEP 35

Stop long tern gas delivery pressure seek mode. This step prevents an increase in pressure where the pressure has corrected the arousal or respiratory event or a recommended maximum pressure value is exceeded.

Finally, it is to be understood that various alterations, modifications and/or additions may be introduced into the constructions and arrangements of parts previously described without departing from the spirit or ambit of the invention.

What is claimed is:

1. An apparatus for controlling gas delivery to a patient to enhance sleep efficiency of the patient during the gas delivery, said apparatus including:

a monitoring component adapted to monitor at least one sleep state physiological variable of a patient during an application of a positive gas pressure to an airway of the patient, to provide monitoring information representing the at least one sleep state physiological variable; and a digital processing component programmed to include a deriving component in communication with the monitoring component, said deriving component comprising a sleep staging algorithm to automatically derive a plurality of sleep states of the patient based on the monitoring information, the plurality of sleep states including at least two sleep states selected from the group comprising sleep stages 1–4, REM, micro-arousal, arousal and wake, corresponding to the at least one sleep state physiological variable;

said digital processing component further including a pressure value determining component receiving said plurality of sleep states to determine a plurality of gas pressure values, each one of the gas pressure values corresponding to each one of the sleep states, said gas pressure values being applicable to control a gas delivery device to control said positive gas pressure in accordance with the gas pressure values.

2. The apparatus according to claim 1 wherein said at least one physiological variable is selected from the group of variables consisting of EEG, EOG, EMG, patient position, and patient breathing.

3. The apparatus according to claim 1 wherein the sleep staging algorithm is adapted for evaluating arousal states.

4. The apparatus according to claim 1 wherein the sleep staging algorithm is adapted for evaluating respiratory events.

5. The apparatus according to claim 1 wherein the determining component includes a pressure seek algorithm.

6. The apparatus according to claim 1 further including a patient state table for storing said data.

7. The apparatus according to claim 1 further including a pressure set look-up table for storing said pressure values.

8. The apparatus according to claim 1 further including an air delivery interface for receiving the gas pressure values, and a gas delivery device operably associated with the interface for delivering a gas to the patient in accordance with the gas pressure values.

9. The apparatus according to claim 1 wherein the sleep state physiological variable of the patient monitored by the monitoring component is the relative patient position.

10. A method for controlling gas delivery to a patient, said delivery being adapted to maintain patient sleep efficiency, said method including monitoring at least one sleep state physiological variable of a patient, to provide monitoring information representing the at least one physiological variable;

using the monitoring information in an automatic sleep staging algorithm to derive, a plurality of sleep states of the patient, including at least two sleep states selected from the group including sleep stages 1–4, REM, micro-arousal, arousal and wake, corresponding to the at least one sleep state physiological variable;

using the plurality of sleep states to determine a plurality of gas pressure values, each one of the gas pressure values corresponding to each of the sleep states, each gas pressure value being optimal with respect to its associated sleep state in that a deviation from the gas pressure represented by the associated gas pressure value signifies a deterioration in the sleep efficiency; and using the gas pressure values to control a delivery of a gas to the patient.

11. The method of claim 10 wherein the control of the delivery of a gas to the patient comprises controlling an application of a positive gas pressure to an airway of the patient.

12. The method according to claim 10 wherein said physiological variable is selected from the group consisting of EEG, EOG, EMG, patient position, and patient breathing.

13. The method according to claim 10 wherein said deriving and said determining are performed using a programmed processing device.

14. The method according to claim 10 wherein said determining comprises using a pressure seek algorithm.

15. The method according to claim 10 wherein said deriving comprises deriving the plurality of sleep states during respective epochs of a monitored period, and storing the data in a patient state table.

16. The method according to claim 10 further including storing the gas pressure values in a pressure set look-up table.

17. An apparatus for controlling the delivery of a gas to a patient in accordance with sleep states of the patient, including:

a monitoring device for monitoring at least one sleep state physiological variable of a patient, a digital processing device coupled to the monitoring device for deriving plurality of sleep states of the patient using an automatic sleep staging algorithm, at least two of the sleep states being selected from the group including sleep stages 1–4, REM, micro-arousal, arousal and wake;

a processor coupled to receive the data and including a pressure set look-up table containing a plurality of gas pressure values, each gas pressure value associated with one of the sleep states;

an interface coupled to the processor to receive the gas pressure values corresponding to the respective states; and a gas delivery device operably associated with the interface to deliver the gas to the patient in accordance with the gas pressure values.

18. The apparatus of claim 17 wherein the gas delivery device includes a CPAP device.

19. An apparatus for controlling gas delivery to a patient to enhance sleep efficiency of the patient during the gas delivery, said apparatus including:

a monitoring component adapted to monitor at least one physiological variable of a patient during an application of a positive gas pressure to an airway of the patient, to provide monitoring information representing the at least one physiological variable, wherein the at least one physiological variable is selected from the group consisting of: brain waves, eye movement, heartbeat, muscle function, and patient position; and a digital processing component programmed to include a deriving component in communication with the monitoring component to receive the monitoring information and, based on the monitoring information, using an automatic sleep staging algorithm to derive a plurality of sleep states of the patient corresponding to the at least one physiological variable; said processing component further including a pressure value determining component receiving said plurality of sleep states, and, based on the sleep states, determining a plurality of gas pressure values, one of the gas pressure values corresponding to each one of the sleep states, said gas pressure values being applicable to control a gas delivery device to control said positive gas pressure in accordance with the gas pressure values.

20. The apparatus according to claim 19, wherein said sleep states are selected from the group including sleep stages 1–4, REM, micro-arousal, arousal and wake.

21. The apparatus according to claim 19 further including an air delivery interface for receiving the gas pressure values, and a gas delivery device operably associated with the interface for delivering a gas to the patient in accordance with the gas pressure values.

22. An apparatus for controlling gas delivery to a patient to enhance sleep efficiency of the patient during the gas delivery, said apparatus including:
   a gas delivery device for an application of a positive gas pressure to an airway of the patient;
   a monitoring component adapted to monitor at least one physiological variable indicative of a sleep state of the patient during the application of the positive gas pressure, to provide monitoring information representing the at least one physiological variable; and
   a digital processing component, said digital processing component programmed to include:
      a sleep state deriving component, comprising an automatic sleep staging algorithm, in communication with the monitoring component to receive the monitoring information and, based on the monitoring information, to derive a plurality of sleep states of the patient corresponding to the at least one physiological variable; and
      a pressure value determining component receiving said sleep states and, based on the sleep states, determining a plurality of gas pressure values for controlling the application of the positive gas pressure, each one of the gas pressure values corresponding to each one of the sleep states.

23. The apparatus of claim 22, wherein the at least one physiological variable is selected from the group consisting of brain waves, eye movement, heartbeat, muscle function, and patient position.

24. The apparatus of claim 22, wherein the automatic sleep staging algorithm is operable to determine probabilities of sleep and wake, percentages of delta, subdelta and beta bands, and an averaged amplitude of waveforms, from the at least one physiological variable.

25. The apparatus of claim 22, wherein the plurality of sleep states are selected from the group consisting of sleep stages 1–4, REM, micro-arousal, arousal and wake.

26. The apparatus of claim 22 wherein the at least one physiological variable monitored by the monitoring component is the relative patient position.

27. An apparatus for controlling gas delivery to a patient to enhance sleep efficiency of the patient during the gas delivery, said apparatus including:
   a gas delivery device for an application of a positive gas pressure to an airway of the patient;
   a monitoring component adapted to monitor relative position of the patient during the application of the positive gas pressure, to provide monitoring information representing relative patient position; and
   a digital processing component, said digital processing component programmed to include:
      a patient position deriving component, comprising a patient position algorithm, in communication with the monitoring component to receive the monitoring information and, based on the monitoring information, to derive a plurality of patient position conditions; and
      a pressure value determining component receiving said patient position conditions and, based on the patient position conditions, determining a plurality of gas pressure values for controlling the application of the positive gas pressure, each one of the gas pressure values corresponding to each one of the patient position conditions.

28. An apparatus for controlling gas delivery to a patient to enhance sleep efficiency of the patient during the gas delivery, said apparatus including:
   a monitoring component adapted to monitor at least one physiological variable of a patient during an application of a positive gas pressure to an airway of the patient, to provide monitoring information representing the at least one physiological variable, wherein the at least one physiological variable is selected from the group consisting of: brain waves, eye movement, heartbeat, muscle function, and patient position; and
   a digital processing component programmed to include a deriving component in communication with the monitoring component to receive the monitoring information and, based on the monitoring information, using an automatic sleep staging algorithm to derive a plurality of sleep slates of the patient corresponding to the at least one physiological variable; and using a patient position algorithm to derive a plurality of patient position conditions corresponding to the patient position, said processing component further including a pressure value determining component receiving said plurality of sleep states and said plurality of patient position conditions, and, based on the sleep states and patient position conditions, determining a plurality of gas pressure values, one of the gas pressure values corresponding to each one of the sleep states, said gas pressure values being applicable to control a gas delivery device to control said positive gas pressure in accordance with the gas pressure values.

* * * * *